US009790284B2

(12) United States Patent
Knopf et al.

(10) Patent No.: US 9,790,284 B2
(45) Date of Patent: Oct. 17, 2017

(54) METHODS FOR INCREASING THERMOGENIC ADIPOCYTES

(71) Applicant: Acceleron Pharma Inc., Cambridge, MA (US)

(72) Inventors: John Knopf, Carlisle, MA (US); Jasbir Seehra, Lexington, MA (US); Ravindra Kumar, Acton, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 0 days.

(21) Appl. No.: 14/242,212

(22) Filed: Apr. 1, 2014

(65) Prior Publication Data

US 2014/0328845 A1  Nov. 6, 2014

Related U.S. Application Data

(63) Continuation of application No. 13/403,657, filed on Feb. 23, 2012, now Pat. No. 8,703,694, which is a continuation of application No. 12/796,332, filed on Jun. 8, 2010, now Pat. No. 8,178,488.

(60) Provisional application No. 61/280,545, filed on Nov. 3, 2009, provisional application No. 61/276,422, filed on Sep. 10, 2009, provisional application No. 61/268,128, filed on Jun. 8, 2009.

(51) Int. Cl.
| | |
|---|---|
| *A61K 38/00* | (2006.01) |
| *A61K 39/395* | (2006.01) |
| *C07K 16/40* | (2006.01) |
| *A61K 31/7088* | (2006.01) |
| *C07K 14/71* | (2006.01) |
| *A61K 38/17* | (2006.01) |

(52) U.S. Cl.
CPC .......... *C07K 16/40* (2013.01); *A61K 31/7088* (2013.01); *A61K 38/1796* (2013.01); *C07K 14/71* (2013.01); *A61K 38/00* (2013.01); *C07K 2319/30* (2013.01)

(58) Field of Classification Search
CPC .................................................. C07K 16/40
See application file for complete search history.

(56) References Cited

U.S. PATENT DOCUMENTS

| | | | |
|---|---|---|---|
| 4,973,577 A | 11/1990 | Vale, Jr. et al. | |
| 5,118,667 A | 6/1992 | Adams et al. | |
| 5,658,876 A | 8/1997 | Crowley et al. | |
| 5,703,043 A | 12/1997 | Celeste et al. | |
| 5,760,010 A | 6/1998 | Klein | |
| 5,808,007 A | 9/1998 | Lee et al. | |
| 5,824,637 A | 10/1998 | Crowley et al. | |
| 5,847,078 A | 12/1998 | Eto et al. | |
| 5,885,794 A | 3/1999 | Mathews et al. | |
| 6,004,780 A | 12/1999 | Soppet et al. | |
| 6,093,547 A | 7/2000 | Jin et al. | |
| 6,132,988 A | 10/2000 | Sugino et al. | |
| 6,162,896 A | 12/2000 | Mathews et al. | |
| 6,287,816 B1 | 9/2001 | Rosen et al. | |
| 6,440,930 B1 | 8/2002 | Rinella, Jr. | |
| 6,451,334 B2 | 9/2002 | Perrine | |
| 6,537,966 B1 | 3/2003 | Duan et al. | |
| 6,548,634 B1 | 4/2003 | Ballinger et al. | |
| 6,599,876 B2 | 7/2003 | Kojima | |
| 6,605,699 B1 | 8/2003 | Ni et al. | |
| 6,632,180 B1 | 10/2003 | Laragh | |
| 6,656,475 B1 | 12/2003 | Lee et al. | |
| 6,656,708 B1 | 12/2003 | Yu et al. | |
| 6,692,925 B1 | 2/2004 | Miyazono et al. | |
| 6,696,260 B1 | 2/2004 | Lee et al. | |
| 6,777,205 B1 | 8/2004 | Carcagno et al. | |
| 6,835,544 B2 | 12/2004 | Mathews et al. | |
| 6,891,082 B2 | 5/2005 | Lee et al. | |
| 7,041,641 B2 * | 5/2006 | Rueger .................. | A61L 31/047 424/486 |
| 7,192,717 B2 | 3/2007 | Hill et al. | |
| 7,202,210 B2 | 4/2007 | Wolfman et al. | |
| 7,261,893 B2 | 8/2007 | Veldman et al. | |
| 7,320,789 B2 | 1/2008 | Dunham et al. | |
| 7,560,441 B2 | 7/2009 | Wolfman et al. | |
| 7,612,041 B2 | 11/2009 | Knopf et al. | |
| 7,709,605 B2 | 5/2010 | Knopf et al. | |
| 7,842,663 B2 | 11/2010 | Knopf et al. | |

(Continued)

FOREIGN PATENT DOCUMENTS

| | | |
|---|---|---|
| EP | 1174149 A1 | 1/2002 |
| EP | 1 362 062 A1 | 11/2003 |

(Continued)

OTHER PUBLICATIONS

Bogdanovich et al., Nature 420: 418-421, 2002.*
Gustafson et al., Arterioscler. Thromb Vasc Biol. 2007, 27: 2276-2283.*
Abaza, M.S.I., et al., "Effects of Amino acid Substitutions Outside an Antigenic Site," J. Protein Chem., 11(5):433-444 (1992).
Abbiotec: ACTR-IIA Antibody: Catalog No. 251303 (http://www.abbiotec.com) Jun. 3, 2010.
Acceleron Pharma Presents Positive Phase 1 Results Demonstrating ACE-011 Increases Markers of Bone Formation, Acceleron Pharma, pp. 1-2, <www.acceleronpharma.com/contents/news/press-releases/detail.jsp/q/news-id/47> Downloaded from the Internet on Feb. 17, 2009.

(Continued)

*Primary Examiner* — Gyan Chandra
(74) *Attorney, Agent, or Firm* — White & Case LLP

(57) ABSTRACT

In certain aspects, the present invention provides compositions and methods for increasing thermogenic adipocytes (e.g., brown adipocytes or other UCP-1 expressing adipocytes) by administering an antagonist of an ActRIIB signaling pathway. Examples of such antagonists include ActRIIB polypeptides, anti-ActRIIB antibodies, anti-myostatin antibodies, anti-GDF3 antibodies, anti-Nodal, anti-activin, and anti-GDF11 antibodies. A variety of metabolic and other disorders may be treated by causing an increase in thermogenic adipocytes.

18 Claims, 15 Drawing Sheets
(14 of 15 Drawing Sheet(s) Filed in Color)

(56) References Cited

U.S. PATENT DOCUMENTS

| | | |
|---|---|---|
| 7,893,213 B2 | 2/2011 | Mathews et al. |
| 7,919,296 B2 | 4/2011 | Wang |
| 7,951,771 B2 | 5/2011 | Knopf et al. |
| 7,988,973 B2 | 8/2011 | Sherman |
| 8,007,809 B2 | 8/2011 | Sherman |
| 8,058,229 B2 | 11/2011 | Seehra et al. |
| 8,067,360 B2 | 11/2011 | Knopf et al. |
| 8,128,933 B2 | 3/2012 | Knopf et al. |
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,881 B2 | 10/2012 | Seehra et al. |
| 8,343,933 B2 | 1/2013 | Knopf et al. |
| 8,388,968 B2 | 3/2013 | Berger et al. |
| 8,629,109 B2 | 1/2014 | Knopf et al. |
| 8,703,694 B2 | 4/2014 | Knopf et al. |
| 8,703,927 B2 | 4/2014 | Seehra et al. |
| 8,765,663 B2 | 7/2014 | Seehra et al. |
| 8,895,016 B2 | 11/2014 | Sherman et al. |
| 2001/0039036 A1 | 11/2001 | Mathews et al. |
| 2002/0082413 A1* | 6/2002 | Spiegelman ....... C07K 14/4702 536/23.5 |
| 2002/0150577 A1* | 10/2002 | Lee .................. C07K 14/51 424/146.1 |
| 2003/0082233 A1 | 5/2003 | Lyons et al. |
| 2003/0083251 A1 | 5/2003 | Westenfelder |
| 2003/0118556 A1 | 6/2003 | Kaspar et al. |
| 2003/0144203 A1 | 7/2003 | Bowen |
| 2003/0215913 A1 | 11/2003 | Alvarez et al. |
| 2003/0224397 A1 | 12/2003 | Lowman et al. |
| 2004/0033511 A1 | 2/2004 | Pfizenmaier et al. |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0239070 A1 | 10/2005 | Von Knebel-Doeberitz et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0172347 A1 | 8/2006 | Mellor et al. |
| 2006/0210657 A1 | 9/2006 | Chou |
| 2007/0048830 A1 | 3/2007 | Gilbert et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0185024 A1* | 8/2007 | Jessell ................. C12N 5/0619 435/325 |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0183624 A1 | 7/2010 | Seehra et al. |
| 2010/0272734 A1 | 10/2010 | Berger et al. |
| 2010/0316644 A1 | 12/2010 | Seehra et al. |
| 2011/0038831 A1 | 2/2011 | Seehra et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2012/0003218 A1 | 1/2012 | Sherman et al. |
| 2012/0015877 A1 | 1/2012 | Seehra et al. |
| 2012/0052067 A1 | 3/2012 | Sherman |
| 2012/0148588 A1 | 6/2012 | Knopf et al. |
| 2012/0156204 A1 | 6/2012 | Seehra et al. |
| 2012/0237521 A1 | 9/2012 | Berger et al. |
| 2013/0004489 A1 | 1/2013 | Knopf et al. |
| 2013/0065299 A1 | 3/2013 | Knopf et al. |
| 2013/0071393 A1 | 3/2013 | Seehra et al. |
| 2013/0177559 A1 | 7/2013 | Seehra et al. |
| 2013/0184210 A1 | 7/2013 | Knopf et al. |
| 2013/0195862 A1 | 8/2013 | Knopf et al. |
| 2013/0243743 A1 | 9/2013 | Seehra et al. |
| 2013/0244324 A1 | 9/2013 | Seehra et al. |
| 2014/0056902 A1 | 2/2014 | Shimizu et al. |
| 2014/0079700 A1 | 3/2014 | Knopf et al. |

FOREIGN PATENT DOCUMENTS

| | | |
|---|---|---|
| EP | 1 416 273 A1 | 5/2004 |
| JP | 2007-099764 A1 | 4/2007 |
| WO | WO-92/04913 A1 | 4/1992 |
| WO | WO-92/20793 A1 | 11/1992 |
| WO | WO 93/00432 A1 | 1/1993 |
| WO | WO-94/15965 A1 | 7/1994 |
| WO | WO-94/26893 A1 | 11/1994 |
| WO | WO-95/10611 A1 | 4/1995 |
| WO | WO-95/29685 A1 | 11/1995 |
| WO | WO-97/23613 A2 | 7/1997 |
| WO | WO 98/18926 A1 | 5/1998 |
| WO | WO-99/06559 A1 | 2/1999 |
| WO | WO-00/18932 A2 | 4/2000 |
| WO | WO 00/25807 A1 | 5/2000 |
| WO | WO-00/43781 A2 | 7/2000 |
| WO | WO-0062809 A1 | 10/2000 |
| WO | WO-01/36001 A2 | 5/2001 |
| WO | WO-01/43763 A1 | 6/2001 |
| WO | WO-02/10214 A2 | 2/2002 |
| WO | WO 02/22680 A2 | 3/2002 |
| WO | WO 02/36152 A1 | 5/2002 |
| WO | WO 02/40501 A2 | 5/2002 |
| WO | WO-02/43759 A2 | 6/2002 |
| WO | WO-02074340 A1 | 9/2002 |
| WO | WO-02/085306 A2 | 10/2002 |
| WO | WO-02/094852 A2 | 11/2002 |
| WO | WO-03/006057 A1 | 1/2003 |
| WO | WO-03/053219 A2 | 7/2003 |
| WO | WO-03/072808 A1 | 9/2003 |
| WO | WO-03087162 A2 | 10/2003 |
| WO | WO-2004016639 A1 | 2/2004 |
| WO | WO-2004/039948 | 5/2004 |
| WO | WO 2004/069237 | 8/2004 |
| WO | WO 2004/086953 A2 | 10/2004 |
| WO | WO 2004/092199 A2 | 10/2004 |
| WO | WO-2004/108157 A2 | 12/2004 |
| WO | WO-2005/003158 A2 | 1/2005 |
| WO | WO-2005/009460 A2 | 2/2005 |
| WO | WO-2005/014650 A2 | 2/2005 |
| WO | WO-2005/028517 A2 | 3/2005 |
| WO | WO-2005053795 A2 | 6/2005 |
| WO | WO-2005/070967 A2 | 8/2005 |
| WO | WO-2005/094871 A2 | 10/2005 |
| WO | WO-2005/097825 A2 | 10/2005 |
| WO | WO-2005/113590 A2 | 12/2005 |
| WO | WO-2006/002387 A2 | 1/2006 |
| WO | WO-2006/012627 A2 | 2/2006 |
| WO | WO-2006/020884 A2 | 2/2006 |
| WO | WO-2006/039400 A2 | 4/2006 |
| WO | WO-2006/083183 A1 | 8/2006 |
| WO | WO-2006/088972 A2 | 8/2006 |

(56) References Cited

FOREIGN PATENT DOCUMENTS

| WO | WO-2006115274 A1 | 11/2006 |
|---|---|---|
| WO | WO-2007/038703 A2 | 4/2007 |
| WO | WO-2007/053775 A1 | 5/2007 |
| WO | WO-2007/062188 A2 | 5/2007 |
| WO | WO-2007/067616 A2 | 6/2007 |
| WO | WO 2007/071023 A1 | 6/2007 |
| WO | WO 2007/075702 A2 | 7/2007 |
| WO | WO-2007/076127 A2 | 7/2007 |
| WO | WO 2007/087505 A2 | 8/2007 |
| WO | WO 2007/101060 A2 | 9/2007 |
| WO | WO-2008/015383 A2 | 2/2008 |
| WO | WO-2008/031061 A2 | 3/2008 |
| WO | WO-2008/060139 A1 | 5/2008 |
| WO | WO-2008/072723 A1 | 6/2008 |
| WO | WO-2008/073292 A2 | 6/2008 |
| WO | WO-2008/076437 A2 | 6/2008 |
| WO | WO-2008/094708 A2 | 8/2008 |
| WO | WO-2008/097541 A2 | 8/2008 |
| WO | WO-2008/100384 A2 | 8/2008 |
| WO | WO-2008/109167 A2 | 9/2008 |
| WO | WO-2008/151078 A8 | 12/2008 |
| WO | WO-2009/009059 A1 | 1/2009 |
| WO | WO-2009/019504 A1 | 2/2009 |
| WO | WO-2009/019505 A2 | 2/2009 |
| WO | WO 2009/021747 A2 | 2/2009 |
| WO | WO-2009/025651 A1 | 2/2009 |
| WO | WO-2009/070243 A2 | 6/2009 |
| WO | WO-2009/137075 A1 | 11/2009 |
| WO | WO-2009/137613 A2 | 11/2009 |
| WO | WO-2009/158015 A2 | 12/2009 |
| WO | WO-2009/158025 A2 | 12/2009 |
| WO | WO-2009/158033 A2 | 12/2009 |
| WO | WO-2010/019261 A1 | 2/2010 |
| WO | WO-2010/083034 A1 | 7/2010 |
| WO | WO-2010/125003 A1 | 11/2010 |
| WO | WO-2010144452 A1 | 12/2010 |
| WO | WO-2010151426 A1 | 12/2010 |
| WO | WO-2011020045 A1 | 2/2011 |
| WO | WO-2011/031901 A1 | 3/2011 |
| WO | WO 2012/027065 A2 | 3/2012 |
| WO | WO-2013006437 A1 | 1/2013 |
| WO | WO 2013/059347 A1 | 4/2013 |
| WO | WO 2013/063536 A1 | 5/2013 |
| WO | WO 2014/066487 A2 | 5/2014 |

OTHER PUBLICATIONS

Acta Cryst., "The CCP4 suite: programs for protein crystallography: Collaborative Computational Project, No. 4," D50: 760-763 91994).
Akel et al, Neutralization of Autocrine Transforming Growth Factor -β in Human Cord Blood CD34$^+$CD38$^-$Lin$^-$ Cells Promotes Stem-Cell-Factor-Mediated Erythropoietin-Independent Early Erythroid Progenitor Development and Reduces Terminal Differentiation. Stem Cells, 21:557-567 (2003).
Akpan, I., et al., "The effects of a soluble activin type IIB receptor on obesity and insulin sensitivity," International Journal of Obesity, 33(11):1265-1273 (2009).
Allendorph, G.P., et al., "Structure of the ternary signaling complex of a TGF-β superfamily member," PNAS, 103(20):7643-7648 (2006).
Anonymous "Learning about Thalassemia" <http://www.genome.gov/10001221> Accessed on Internet Jul. 9, 2013.
Anonymous "Iron and Thalassemia," Accessed on the Internet Apr. 3, 2014 at <sickle.bwh.harvard.edu/thaliron.html>. Published Aug. 25, 1997.
Anti-ActRIIA Antibodies: Commercial Monoclonal Antibodies Against Human ActRIIA (2010).
Antibodies for ACVR2A: <http://www.genecards.org/cgi-bin/card-disp.pl?gene=Acvr2a> (Jun. 8, 2010).
Attie et al., "A Single Ascending-Dose Study of Muscle Regulator Ace-031 in Healthy volunteers," Muscle & Nerve, pp. 1-8 (2012).
Banks, G.B., et al., "The Value of Mammalian Models for Duchenne Muscular Dystrophy in Developing Therapeutic Strategies," Current Topics in Developmental Biology, 84:431-453 (2008).
Benny Klimek, Margaret E., et al., "Acute inhibition of myostatin-family proteins preserves skeletal muscle in mouse models of cancer cachexia," Biochemical and Biophysical Research Communications, 391:1548-1554 (2010).
Berenson, J.R., "Multiple Myeloma," Multiple Myeloma: Plasma Cell Disorders: Merck Manual Professional, pp. 1-5, Jul. 2008.
Bhatia et al., Protein Glycosylation: Implications for In Vivo Functions and Therapeutic Applications. Advances in Biochemical Engineering/Biotechnology, vol. 64: 155-201 (1998).
Binkert, et al., "Cloning, sequence analysis and expression of a cDNA encoding a novel insulin-like growth factor binding protein (IGFBP-2)," The EMBO Journal, 8(9):2497-2502 (1989).
Bodey, B., et al., "Failure of Cancer Vaccines: The Significant Limitations of this Approach to Immunotherapy," Anticancer Research, 20:2665-2676 (2000).
Bogdanovich, S., et al., "Functional improvement of dystrophic muscle by myostatin blockade," Nature, 420:418-421 (2002).
Bork, "Powers and Pitfalls in Sequence Analysis: The 70% Hurdle," Genome Research, 10:398-400 (2000).
Bowie, J.U., et al., "Deciphering the Message in Protein Sequences: Tolerance to Amino Acid Substitutions," Science, 257:1306-1310 (1990).
Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., Activin A mediates growth inhibition and cell cycle arest through Smads in human breast cancer cells. Cancer Research, 65(17):7968-7975; Abstract (2005).
Burgess, W.H., et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," J. Cell Biol., 111:2129-2138 (1990).
Cadena, S.M., et al., "Administration of a Soluble Activin Type IIB Receptor Promotes Skeletal Muscle Growth Independent of Fiber Type," Journal of Applied Physiology, 109:635-642 (2010).
Cannon and Nedergaard, :Neither fat nor flesh, Nature, vol. 454(7207):947-948 (2008).
Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).
Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2007).
Centrella et al., "Activin-A Binding and Biochemical Effects in Osteoblast-Enriched Cultures from Fetal-Rat Parietal Bone," Molecular and Cellular Biology, 11(1):250-58 (1991).
Chamberlain, R.S., et al., "Innovations and strategies for the development of anticancer vaccines," Expert Opinion on Pharmacotherapy, 1(4):603-614 (2000).
Chamow, S.M., and Ashkenazi, A., "Immunoadhesins: Principles and Applications," TIBTECH, 14: 52-60 (1996).
Chang, Sam S., "Exploring the Effects of Luteinizing Hormone-Releasing Hormone Agonist Therapy on Bone Health: Implications in the Management of Prostate Cancer," Urology, vol. 52: 29-35 (2003).
Chapman, B., et al., "Effect of intron a from human cytomegalovirus (Towne) immediate-early gene on heterologous expression in mammalian cells," Nucleic Acids Research, 19(14):3979-3986 (1991).
Chardès et al., "Efficient amplification and direct sequencing of mouse variable regions from any immunoglobulin gene family," FEBS Lett. vol. 452(3): 386-394 (1999).
Chavez-Tapia, Norberto-C et al., "Insulin sensitizers in treatment of nonalcoholic fatty liver disease: Systematic review," World Journal of Gastroenterology, vol. 12(48): 7826-7831 (2006).
Chen, Y.G., et al. "Regulation of Cell Proliferation, Apoptosis, and Carcinogenesis by Activin," Exp. Biol. Med., 227(2):75-87 (2002).

(56) References Cited

OTHER PUBLICATIONS

Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Cirillo et al., "Hematocrit, blood pressure, and hypertension. The Gubbio Population Study," Hypertension, 20(3):319-326 (1992).
Coerver, et al., "Activin Signaling through Activin Receptor Type II Causes the Cachexia-Like Symptoms in Inhibin-Deficent Mice," 10(5):534-543 (1996).
Collins, C.D., "Multidisciplinary Symposium: Haematological Malignancies," Cancer Imaging 5:S119-S126 (2005).
Colman, P.M., et al., "Effects of amino acid sequence changes on antibody-antigen interactions," Research of Immunology, 145(1):33-36 (1994).
Crisan et al., "A Reservoir of Brown Adipocyte Progenitors in Human Skeletal Muscle," Stem Cells, vol. 26(9):2425-2433 (2008).
Daluiski et al., "Bone Morphogenetic Protein-3 is a Negative Regulator of Bone Density," Nature Genetics, 27:84-88 (2001).
Database Geneseq [Online], "Variable heavy chain of anti-human Fas ligand antibody NOK-4," retrieved from EBI accession No. GSP:AAW00829; Database accession No. AAW00829; abstract, sequence (1997).
Database Geneseq [Online]; "Monoclonal antibody 10D4 HMGB1 Vkappa domain," retrieved from EBI accession No. GSP:ADY85028, Database accession No. GSP:ADY85028; abstract, sequence (2005).
Deal, C., "Potential New Drug Targets for Osteoporosis," Nature Clinical Practice, 5(1):20-27 (2009).
Deconinck, N., et al., "Pathophysiology of Duchenne Muscular Dystrophy: Current Hypotheses," Pediatr. Neurol., 36:1-7 (2007).
del Re et al., "Reconstitution and Analysis of Soluble Inhibin and Activin Receptor Complexes in a Cell-free System," The Journal of Biological Chemistry, 279(51):53126-53135 (2004).
Delogu, G., et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).
DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).
Donald et al., "SDR: a database of predicted specificity-determining residues in proteins," Nucleic Acids Research, vol. 37: D191-D194 (2009).
Donaldson, et al., "Activin and inhibin binding to the soluble extracellular domain of activin receptor II", Endocrinology 140(4):1760-1766 (1999).
Donaldson, et al., "Molecular Cloning and Binding Properties of the Human Type II Activin Receptor", Biochemical and Biophysical Research Communications, 184(1):310-316 (1992).
Eijken, M., "The Activin A-Follistatin System: Potent Regulator of Human Extracellular Matrix Mineralization," The FASEB Journal, 21:2949-2960 (2007).
Elliot et al., "Enhancement of therapeutic protein in vivo activities through glycoengineering," Nature Biotechnology, vol. 21: 414-421 (2003).
Fafioffe, et al., "Activin and inhibin receptor gene expression in the ewe pituitary throughout the oestrous cycle," Journal of Endocrinology, 182:55-68 (2004).
Fajardo, R. J., et al., "Treatment with a Soluble Receptor for Activin Improves Bone Mass and Structure in the Axial and Appendicular Skeleton of Female Cynomolgus Macaques (*Macaca fascicularis*)," Bone, 46:64-71 (2010).
Fan, et al., "Preclinical evaluation of Hematide, a novel erythropoiesis stimulating agent, for the treatment of anemia," Experimental Hematology 34, pp. 1303-1311 (2006).
Farmer, Stephen R., "Brown Fat and Skeletal Muscle: Unlikely Cousins?," Cell, vol. 134(5):726-727 (2008).

Foucar, K., Myelodysplastic/Myeloproliferative Neoplasms, Am J Clin Pathol, vol. 132: 281-289 (2009).
Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).
Frigon, N.L., et al, "Regulation of Globin Gene Expression in Human K562 Cells by Recombinant Activin A," Blood, 79(3):765-772 (1992).
Fuller et al., "Activin A is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).
GenBank NM_001106, *Homo sapiens* activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gilbert, R., et al., "Prolonged dystrophin expression and functional correction of mdx mouse muscle following gene transfer with a helper-dependent (gutted) adenovirencoding murine dystrophin," Human Molecular Genetics, 12(11)1287-1299 (2003).
Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).
Gonzalez-Cadavid, N.F., et al., "Organization of the human myostatin gene and expression in healthy men and HIV-infected men with muscle wasting," PNAS, 95:14938-14943 (1998).
Gray, et al., "Identification of a binding site on the type II activin receptor for activin and inhibin", Journal of Biological Chemistry, 275(5):3206-3212(2000).
Greenspan, N.S., et al., "Defining epitopes: It's not as easy as it seems," Nature Biotechnology, 17:936-937 (1999).
Greenwald, et al., "Characterization of the Extracellular Ligand-Binding Domain of the Type II Activin Receptor," Biochemistry, 37(47):16711-16718 (1998).
Greenwald, et al., "The BMP7/ActRII Extracellular Domain Complex Provides New Insights into the Cooperative Nature of Receptor Assembly," Molecular Cell, 11:605-617 (2003).
Greenwald, J., et al., "Three-finger toxin fold for the extracellular ligand-binding domain of the type II activin receptor serine kinase," Nature Structural Biology, 6(1):18-22 (1999).
Gregoriadis, G., et al., "Polysialic acids: potential in drug delivery," FEBS, 315(3):271-276 (1993).
Guo, et al., Protein Tolerance to Random Amino Acid Change. Proc. Natl. Acad. Sci. USA, 101(25):9205-9210 (Jun. 22, 2004). Epub Jun. 14, 2004.
Gupta, V. et al., "Transforming Growth Factor-b Superfamily: Evaluation as Breast Cancer Biomarkers and Preventive Agents," Current Cancer Drug Targets, 4:165-182 (2004).
Gura, T., "Cancer Models: Systems for Identifying New Drugs Are Often Faulty," Science, 278(5340):1041-1042 (1997).
Haidar et al., "Paraspinal extramedullary hematopoiesis in patients with thalassemia intermedia," Eur Spine J., vol. 19: 871-878 (2010).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).

(56) References Cited

OTHER PUBLICATIONS

Hamrick, M.W., et al., "Femoral Morphology and Cross-sectional Geometry of Adult Myostatin-deficient Mice," Bone, 27(3):343-349 (2000).
Harousseau et al., "Multiple Myeloma," American Society of Hematology, pp. 237-256 (2004).
Harrison, C.A., et al., "An Activin Mutant with Disrupted ALK4 Binding Blocks Signaling via Type II Receptors," The Journal of Biological Chemistry, 279(27):28036-28044 (2004).
Harrison, et al., "Antagonists of activin signaling: mechanisms and potential biological applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, A., et al., "A truncated activin receptor inhibits mesoderm induction and formation of axial structures in Xenopus embryos," Nature, 359:609-614 (1992).
Herbert, W.J., et al., The Dictionary of Immunology, Academic Press, 3rd Edition, London, pp. 58-59 (1985).
Hilden, K., et al., "Expression of Type II Activin Receptor Genes During Differentiation of Human K562 Cells and cDNA Cloning of the Human Type IIB Activin Receptor," Blood, 83(8):2163-2170 (1994).
Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Holm et al., "Functional mapping and single chain construction of the anti-cytokeratin 8 monoclonal antibody TS1," ScienceDirect; Molecular Immunology, vol. 44(6): 1075-1084 (2007).
Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).
Human Activin RIIA Antibody, R&D Systems, Tools for Cell Biology Research, Catalog No. MAB340 (Rev Mar. 22, 2011).
Ikenoue et al., "Inhibitory Effects of Activin-A on Osteoblast Differentiation During Cultures of Fetal Rat Calvarial Cells," Journal of Cellular Biochemistry, 75:206-214 (1999).
"The Illustrated Guide to Bone Marrow Diagnosis Second Edition," Ed. By G. Kumar. Originally published 2003.
International Search Report, PCT/2010/037779, dated Oct. 8, 2010.
Ito et al., "Presence of activin signal transduction in normal ovarian cells and epithelial ovarian carcinoma," British Journal of Cancer, vol. 82(8): 1415-1420 (2000).
Kaiser, J., "First Pass at Cancer Genome Reveals Complex Landscape," Science, 313:1370 (2006).
Kaspar, B.K., et al., "Retrograde Viral Delivery of IGF-1 Prolongs Survival in a Mouse ALS Model," Science, 301:839-842 (2003).
Kim, et al., "Type IIa IgG-Fc Fusion Protein, Increases Hemoglobin and Hematocrit Levels in Postmenopausal Healthy Women," Blood, 112(11):1316 (2008).
Knight, "Roles of Inhibins, Activins, and Follistatin in the Female Reproductive System," Frontiers in Neuroendocrinology, 17:476-509 (1996).
Koncarevic et al., "A Soluble Activin Receptor Type IIB Prevents the Effects of Angdrogen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF-b Family in Osteoclastogenesis Induced by RANKL," Cellular Signaling, 14:31-36 (2002).
Krag, T.O.B., et al., "Heregulin ameliorates the dystrophic phenotype in mdx mice," PNAS, 101(38):13856-13860 (2004).

Krneta, J., et al., "Dissociation of Angiogenesis and Tumorigenesis in Follistatin- and Activin-Expressing Tumors," Cancer Research, 66(11):5686-5695 (2006).
Krystal et al., Transforming Growth Factor β1 is an Inducer of Erythroid Differentiation. J. Exp. Med. vol. 180 pp. 851-860 (1994).
Kubanek, B., "Introduction: The Role of the Microenvironment and Cytokines on the Modulation of Erythropoiesis," Annals New York Academy of Sciences, pp. 257-258 (1994).
Kumar, T.R., et al., "Regulation of FSHβ and GnRH Receptor Gene Expression in Activin Receptor II Knockout Male Mice," Mol. Cell. Endocrinol., 212(1-2):19-27 (2003).
Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-based strategies for drug design and discovery," Science, 257(5073):1078-1082 (1992).
Lazar, E., et al., "Transforming Growth Factor α: Mutation of Aspartic Acid 47 and Leucine 48 Results in Different Biological Activities," Molecular and Cellular Biology, 8(3):1247-1252 (1988).
Lazar, Mitchell A., "How Now, Brown Fat?" Science, vol. 321(5892):1048-1049 (2008).
Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23(2):117-122 (2006).
Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Lifespan Biosciences, Activin Receptor Type 2A (ACVR2A) Mouse anti-Human Monoclonal Antibody—LS-C33835—LifeSpan Biosciences, (2010).
Liu et al., "Characterization of isoforms of activin receptor-interacting protein 2 that augment activin signaling," Journal of Endocrinology, vol. 189: 409-421 (2006).
Lotinun, S., et al., "A Soluble Activin Receptor Type IIA Fusion Protein (ACE-011) Increases Bone Mass Via a Dual Anabolic-Antiresorptive Effect in Cynomolgus Monkeys," Bone, 46:1082-1088 (2010).
Lu, S., et al., "Simian Immunodeficiency Virus DNA Vaccine Trial in Macaques," Journal of Virology, 70(6):3978-3991 (1996).
Ludlow, H., et al., "Development of a new antibody to the human inhibin/activin βB subunit and its application to improved inhibin B ELISAs," J. Immunol. Methods, 329:102-111 (2008).
Ma, "Animal Models of Disease," Modern Drug Discovery, 30-36 (2004).
MacCallum et al., "Antibody-antigen Interactions: Contact Analysis and Binding site Topography," J. Mol. Biol, vol. 262: 732-745 (1996).
Maguer-Satta, V., et al, "A Novel Role for Fibronectin Type 1 Domain in the Regulation of Human Hematopoietic Cell Adhesiveness Through Binding to Follistatin Domains of FLRG and Follistatin," Experimental Cell Research, Academic Press, 312(4):434-442 (2006).
Maguer-Satta, V., et al, "Regulation of human erythropoiesis by activin A, BMP2, and BMP4, members of the TGFβ family," Experimental Cell Research, 282:110-120 (2003).
Maguer-Satta, V., et al., "FLRG, Member of the Follistatin Family, a New Player in Hematopoiesis," Molecular and Cellular Endocrinology, Elsevier Ireland Ltd., 225(1-2):109-118 (2004).

(56) References Cited

OTHER PUBLICATIONS

Mathews, L.S., et al., "Expression Cloning of an Activin Receptor, a Predicted Transmembrane Serine Kinase," Cell, 65(6):973-982 (1991).
Matzuk et al., "Cloning of the human activin receptor cDNA reveals high evolutionary conservation," Biochim Biophys Acta, 1130(1):105-108 (1992).
Matzuk et al., "Different phenotypes for mice deficient in either activins or activin receptor type II," Nature, 374:356-360 (1995).
McCarthy et al., Monoclonal antibodies that recognize the type-2 activin receptor, ACTR2, Hybridoma, vol. 13(3):199-203 (1994) (abstract).
McNally, E.M., "Powerful Genes—Myostatin Regulation of Human Muscle Mass," N. Engl. J. Med., 350(26):2642-2644 (2004).
McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).
McPherron, A.C., et al., "Regulation of Skeletal Muscle Mass in Mice by a Bew TGF-b Superfamily Member," Nature, 387:83-90 (1997).
McPherron and Lee, "Suppression of body fat accumulation in myostatin-deficient mice," The Journal of Clinical Investigation, vol. 109(5):595-601 (2002).
McPherson, S.J., et al., "Growth inhibitory response to activin A and B by human prostate tumour cell lines LNCaP and DU1465", Journal of Endocrinology, 154:535-545 (1997).
Menstruation: Absent Periods (Amenorrhea), Website downloaded on Jun. 14, 2010, <http://adam.about.com/reports/000101_2.htm?p=1> (11 pages).
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch13 0d.html> pp. 1-2.
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).
Mickle, et al., "Genotype-Phenotype Relationships in Cystic Fibrosis," Med. Clin. North Am., 84(3):597-607 (2000).
Miller et al., Ligand binding to proteins: the binding landscape model. Protein Sci., 6(10):2166-79 (1997).
Miura, P., et al., "Utrophin upregulation for treating Duchenne or Becker muscular dystrophy: how close are we?," Trends in Molecular Medicine, 12(3):122-129 (2006).
"Monoclonal Anti-human Activin RII Antibody," R&D Systems, Catalog No. MAB3391 (Feb. 18, 2009).
Morrison et al., "A soluble activin type IIB receptor improves function in a mouse model of amyotrophic lateral sclerosis," Experimental Neurology, vol. 217:258-268 (2009).
Mosekilde, L., et al., "Emerging Anabolic Treatments in Osteoporosis," Current Drug Safety, 6:62-74 (2011).
Murase et al., "Possible Involvement of Protein Kinases and Smad2 Signaling Pathways on Osteoclast Differentiation Enhanced by Activin A," Journal of Cellular Physiology, 188:236-242 (2001).
Murata, T., et al., "Anti-activin A Antibody (IgY) Specifically Neutralizes Various Activin A Activities," Proceedings of the Society for Experimental Biology & Medicine, 211(1):100-107 (1996).
Nagamine et al., "Immunohistochemical Detection of Activin A, Follistatin, and Activin Receptors during Fracture Healing in the Rat," Journal of Orthopaedic Research, 16:314-321 (1998).
Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).

Nemeth, E., "Hepcidin in β-thalassemia," Annals of the New York Academy of Sciences, vol. 1202: 31-35. Published Aug. 2, 2010.
Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).
NIH website downloaded May 28, 2014 from: web.archive.org/web/20030409091558/http://www.cc.nih .gov/ccc/patient_education/pepubs/subq.pdf; Patient Information Publications: Giving a Subcutaneous Injection ( 6 pages total).
Ogawa et al., "Bovine Bone Activin Enhances Bone Morphogenetic Protein-Induced Ectopic Bone Formation," The Journal of Biological Chemistry, 267(20):14233-14237 (1992).
Oh, S.P., et al., "Activin type IIA and IIB receptors mediate Gdf11 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Padlan et al., "Identification of specificity-determining residues in antibodies," The FASEB Journal, vol. 9:133-139 (1995).
Patel, K., et al., "The function of Myostatin and strategies of Myostatin blockade—new hope for therapies aimed at promoting growth of skeletal muscle," Neuromuscular Disorders, 15:117-126 (2005).
Paul, William E., Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (*Callithrix jacchus*), Database Biosis, Biosciences Information Service, Accession No. PREV201200750016; Faseb Journal, vol. 22, Experimental Biology Annual Meeting, San Diego, CA (Apr. 5-9, 2008) (Abstract).
Pearsall, et al., "A Soluble Activin Receptor Type IIA (ACTRIIA) Acts as a Novel Bone Anabolic Agent," The Official Journal of the European Calcified Tissue Society, 34th Europena Symposium on Calcified Tissues, (May 2007).
Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).
Pearsall, R.S., et al., "A soluble activin Type IIA receptor induces bone formation and improves skeletal integrity", PNAS, 105(9):7082-7087 (2008).
Perrien, D. S., et al., "Inhibin A is an Endocrine Stimulator of Bone Mass and Strength," Endocrinology, 148(4):1654-1665 (2007).
Phillips, A.J., "The challenge of gene therapy and DNA delivery," J. Pharm. Pharmacology, 53:1169-1174 (2001).
Pirollo, K.F., et al., "Targeted Delivery of Small Interfering RNA: Approaching Effective Cancer Therapies," Cancer Res., 68(5):1247-1250 (2008).
Qi, et al., "Blockade of type β transforming growth factor signaling prevents liver fibrosis and dysfunction in the rat," PNAS, 96:2345-2349 (1999).
Raju, T.S., "Glycosylation in the Fc domain of IgG increases resistance to proteolytic cleavage by papain," Biochemical and Biophysical Research Communications, 341:797-803 (2006).
R&D Systems Catalogue No. AF339 Datasheet: Human Activin RIIB Antibody [retrieved on Feb. 13, 2013] Retrieved from the Internet: http://www.rndsystems.com/pdf/af339.pdf.
Rebbapragada, et al., "Myostatin Signals Through a Transforming Growth Fact b-Like Signaling Pathway to Block Adipogenesis," Molecular and Cellular Biology, 23(20):7230-7242 (2003).
"Recombinant Human Activin RIIA/Fc Chimera," R&D Systems 340-R2 (Aug. 27, 2003).
"Recombinant Human Activin RIIB/Fc Chimera," R&D Systems 339-RB/CF (Aug. 27, 2003).
Reis, F.M., et al., "Activin, Inhibin and the Human Breast," Molecular and Cellular Edocrinology, 225:77-82 (2004).
Risbridger, G.P, et al., "Activins and Inhibins in Endocrine and Other Tumors," Endocrine Reviews, 22(6):836-858 (2001).
Robinson, G.W., et al., "Inhibins and Activins Regulate Mammary Epithelial Cell Differentiation Through Mesenchymal-epithelial Interactions," Development, 124:2701-2708 (1997).

(56) References Cited

OTHER PUBLICATIONS

Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).
Rosenzweig et al., "Cloning and characterization of a human type II receptor for bone morphogenetic proteins," PNAS, 92:7632-7636 (1995).
Ruckle et al., "Single-Dose, Randomized, Double-Blind, Placebo-Controlled Study of ACE-011 (ACTRIIA-IgG1) in Postmenopausal Women," Journal of Bone and Mineral Research, vol. 24(4), pp. 744-752 (2009).
Ruzek et al. Minimal Effects on Immune Parameters Following Chronic Anti-TGF-β Monoclonal Antibody Administration to Normal Mice. Immunopharmacology and Immunotoxicology, 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., The Measurement of Activin/EDF in Mouse Serum: Evidence for Extragonadal Production. Biochecmical and Biophysical Research Communications, 188(2):921-926 (1992).
Sakai, et al., "Osteogenic Activity of Activin in Young Normal Rats and Young Adult and Aged Rats after Ovariectomy," Bone 23:(Suppl.) 467 (1998).
Sako, D., et al., "Characterizationof the Ligand Binding Functionality of the Extracellular Domain of Activin Receptor Type IIB," The Journal of Biological Chemistry, 285(27):21037-21048 (2010).
Satoh, et al., "Hemodynamic changes by recombinant erythropoietin therapy in hemodialyzed patients," Hypertension, 15(3):262-266 (1990).
Schmelzer, C.H., et al., "Purification and Characterization of Recombinant Human Activin B," Biochimica et Biophysica Acta, 1039(2):135-141 (1990).
Schuelke, M., et al., "Myostatin Mutation Associated with Gross Muscle Hypertrophy in a Child," New England Journal of Medicine, 350(26):2682-2688 (2004).
Seale et al., "PRDM16 controls a brown fat/skeletal muscle switch," Nature, vol. 454(7207):961-967 (2008).
Shao, L., et al., "Effect of Activin A on Globin Gene Expression in Purified Human Erythroid Progenitors," Blood, 79(3):773-781 (1992).
Shao, L., et al., "Efficient synthesis of globoside and isoglobside tetrasaccharides by using beta (1->3) N-acetylgalactosaminyltransferase/UDP-N-acetyglucosamine C4 epimerase fusion protein," Chem Commun.: 1422-1423 (2003).
Shapiro et al., "Side Effects of Adjuvant Treatment of Breast Cancer," New England Journal of Medicine, vol. 344: 1997-2008 (2001).
Shav-Tal, Y., et al., "The Role of Activin A in Regulation of Hemopoiesis," Stem Cells, 20:493-500 (2002).
Shi et al., "Energy Balance, Myostatin, and GILZ: Factors Regulating Adipocyte Differentiation in Belly and Bone," PPAR Research, pp. 1-12 (2007).
Shiozaki, M., et al, "Activin A: A Commitment Factor in Erythroid Differentiation," Biochemical and Biophysical Research Communications, 242:631-635 (1998).
Shiozaki, M., et al, "Evidence for the participation of endogenous activin A/erythroid differentiation factor in the regulation of erythropoiesis," Proc. Natl. Acad. Sci. USA, 89:1553-1556 (1992).
Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shoji et al., "Identification and Characterization of a PDZ Protein That Interacts with Activin Type II Receptors," The Journal of Biological Chemistry, vol. 275(8): 5485-5492 (2000).
Shuto et al., "Osteoblasts Express Types I and II Activin Receptors During Early Intramembranous and Endochondral Bone Formation," Journal of Bone Mineral Research, 12(3):403-411 (1997).
Smith, L. et al., "The analysis of doxorubicin resistance in human breast cancer cells using antibody microarrays," Mol. Cancer Therapy, vol. 5: 2115-2120 (2006).
Smith, L. et al., The Status, Quality, and Expansion of the NIH Full-Length cDNA Project: The Mammalian Gene Collection (MGC), Genome Res., vol. 14(10b),: 2127-2127 (2004).
Song, J., et al., "The Type II Activin Receptors Are Essential for Egg Cylinder Growth, Gastrulation, and Rostral Head Development in Mice," Development Biology, 213:157-169 (1999).
Springer, et al., "Seventh European Congress on Clinical and Economic Aspects of Osteoporosis and Osteoarthritis," Osteoporosis International, 18(1):S29-S75 (2007).
Sun, et al., "FSH Directly Regulates Bone Mass," Cell, 125:247-260 (2006).
Supplementary European Search Report—EP 10 78 6694, dated Oct. 23, 2013.
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010.
Swanson et al., "Use of Biosensors to Monitor the Immune Response," Biologics, vol. 109: 71-78 (2000).
Swanson, S. J., "New Technologies for the Detection of Antibodies to Therapeutic Proteins," Immunogenicity of Therapeutics Biological Products, vol. 112: 127-133 (2003).
Tanno, T. and Miller, J.L., "Iron Loading and Overloading due to Ineffective Erythropoiesis," Advances in Hematology, Article ID 358283, Chapter 2 (Abstract) (2010).
Thompson, et al., "Structures of an ActRIIB: activin A complex reveal a novel binding mode for TGF-beta ligand: receptor interactions", EMBO 22(7):1555-1566 (2003).
Thompson, T.B., et al., "Beta A versus beta B: is it merely a matter of express?," Molecular and Cellular Endocrinology, 225:9-17 (2004).
Thorpe and Swanson, "Current methods for Detecting Antibodies against Erythropoietin and Other Recombinant Proteins," Clinical and Diagnostic Laboratory Immunology, vol. 12(1): 28-39 (2005).
Tinsley, J., et al., "Expression of full-length utrophin prevents muscular dystrophy in mdx mice," Nature Medicine, 4(12):1441-1444 (1998).
Tisdale, M.J., "Cachexia in Cancer Patients," Nat. Rev. Cancer, 2:862-87 (2002).
Tokuriki, N., et al., "Stability effects of mutations and protein evolvability," Current Opinion in Structural Biology, 19:596-604 (2009).
Trivedi, R., et al., "Investigational Anabolic Therapies for Osteoporosis," Expert Opin. Investig. Drugs, 19(8):995-1005 (2010).
Truska et al., "Bone morphogenetic proteins 2, 4, and 9 stimulate murine hepcidin 1 expression independently of Hfe, transferrin receptor 2 (Tfr2), and IL-6," PNAS, vol. 103(27):10289-10293 (2006).
Tseng, Yu-Hua et al., "New role of bone morphogenetic protein 7 in brown adipogenesis and energy expenditure," Nature: International Weekly Journal of Science (and Supplementary Information), vol. 454(7207): 1000-1004 (2008).
Tsuchida, et al., "Activin isoforms signal through type I receptor serine/threonine kinase ALK7," Molecular and Cellular Endocrinology, 220:59-65 (2004).

(56) References Cited

OTHER PUBLICATIONS

Tu, P., et al., "Genetic Disruption of Myostatin Reduces the Development of Proatherogenic Dyslipidemia and Atherogenic Lesions in Ldlr Null Mice," Diabetes, 58:1739-1748 (2009).
Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.
Ukkola, et al., "Adiponectin: A Link Between Excess Adiposity and Associated Comorbidities?", Journal of Molecular Medicine, 80(11):696-702 (2002).
US Biological, Activin Receptor Type IIA (RIIA) A0856-05E www.usbio.net/technicalsheet.php?item=A0856-05E dated Jun. 8, 2010.
Utzschneider, et al., The Role of Insulin Resistance in Nonalcoholoc Fatty Liver Disease, J. Clin. Endocrinol. Metab., 944908462_11(12):4753-4761 (Dec. 2006). Epub Sep. 12, 2006.
Vallet, S., et al., "Activin A promotes multiple myeloma-induced osteolysis and is a promising target for myeloma bone disease," PNAS, 107(11):5124-5129 (2010).
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Vidal, L., et al., "Making sense of antisense," European Journal of Cancer, 41:2812-2818 (2005).
Wagner, K.R., et al., "A Phase I/II trial of MYO-029 in Adult Subjects with Muscular Dystrophy," Ann. Neurol., 63:561-571 (2008).
Wagner, K.R., et al., "Loss of Myostatin Attenuates Severity of Muscular Dystrophy in mdx Mice," Ann. Neurol., 52:832-836 (2002).
Wagner, K.R., et al., "Muscle regeneration in the prolonged absence of myostatin," PNAS, 102(7):2519-2524 (2005).
Walsh, F. S, et al., "Myostatin: a modulator of skeletal-muscle stems cells," Biochemical Society Transactions, 33(Pt.6):1513-1517 (2005).
Wang, et al., A single amino acid determines lysophospholipid specificity of the S1P1 (EDG1) and LPA1 (EDG2) phospholipid growth factor receptors. JBC 276:49213-49220 (2001).
Wang, W., et al., "GDF-3 is an adipogenic cytokine under high fat dietary condition," Biochemical and Biophysical Research Comm., 321(4):1024-1031 (2004).
Ward, R., "An update on disordered iron metabolism and iron overload," Hematology, vol. 15(5): 311-317 (2010).
Weber, et al., A slient H-bond can by mutationally activated for high-affinity interaction of BMP-2 and activin type IIB receptor, BMC Structural Biology, 7(6):1-20 (2007).
Wells, J.A., "Additivity of Mutational Effects in Proteins," Biochemistry, 29(37):8509-8517 (1990).
Welt, et al., "Activin: an endocrine or panacrine agent?," European Journal of Endocrinology 139:469-471 (1998).
Wiater, et al., "Inhibin is an Antagonist of Bone Morphogenetic Protein Signaling," The Journal of Biological Chemistry, 278(10):7934-7941 (2003).
Wolfman, N.M., et al., "Activation of latent myostatin by the BMP-1/tolloid family of metalloproteinases," PNAS, 100(26):15842-15846 (2003).
Wong et al., "Validation parameters for a novel biosensor assay which simultaneously measures serum concentrations of a humanized monoclonal antibody and detects induced antibodies," Journal of Immunological Methods, vol. 209: 1-15 (1997).
Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567) (2012). (translated).
Yokota, T., et al., "Isolation and characterization of a mouse cDNA clone that expresses mast-cell growth-factor activity in monkey cells," Proc. Natl. Acad. Sci. USA, 81:1070-1074 (1984).

Yu et al., "Specific roles of activin/inhibin in human erythropoiesis in vitro." Annals New York Academy of Sciences, 20(10):1243-1246 (1991).
Yu, J., et al., "Importance of FSH-releasing protein and inhibin in erythrodifferentiation," Nature, 330:765-767 (1987).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhao, B., et al., "Transgenic expression of myostatin propeptide prevents diet-induced obesity and insulin resistance," Biochemical and Biophysical Research Communications, 337:248-255 (2005).
Zhang et al., Effects of Activin A on the Activities of the Mouse Peritoneal Macrophages, Cellular & Molecular Immunology, vol. 2(1): 63-67 ( 2005).
Abrahams, B. and Ertel, S., 'Acceleron Pharma at Wells Fargo Healthcare Conference—Final', published on Jun. 17, 2014, Fair Disclosure Wire (Quarterly Earnings Reports), Accession No: 32U3101469591FDW.
Acceleron, 'Review of the Data Presented at the European Hematology Association 19th Annual Meeting', considered published on Jun. 16, 2014; Retrieved on Aug. 20, 2015.
Acceleron, 'Corporate Overview', considered published in Jul. 31, 2014, Retrieved on Aug. 20, 2015.
Anti-human Activin RIIA Antibody, R&D Systems, Catalog No. AF340 (Feb. 14, 2006).
Biosis Accession No. 2015:276893 & Piga, A. et al., 'ACE-536 Increases Hemoglobin and Decreases Transfusion Burden and Serum Ferritin in Adults with Beta-Thalassemia: Preliminary Results from a Phase 2 Study', Blood, vol. 124, No. 21, p. 53 (Dec. 6, 2014).
Carrancio, S. et al. "An activin receptor IIA ligand trap promotes erythropoiesis resulting in a rapid induction of red blood cells and haemoglobin," British Journal of Haematology, vol. 165: 870-882 (2014).
Chantry et al., "Inhibiting Activin-A Signaling Stimulates Bone Formation and Prevents Cancer-Induced Bone Destruction in Vivo," Journal of Bone and Mineral Research, vol. 25(12): 2357-2370 (2010).
Donaldson et al., GenBank: BAA06548.1: activin typell A receptor precursor [*Homo sapiens*] (1992).
Dussiot et al., "An activin receptor IIA ligand trap corrects ineffective erythropoiesis in B-thalassemia," Nature Medicine, vol. 20: 398-407 (2014).
Ear et al., "RAP-011 Efficiently Rescues Erthropoiesis in Zebrafish Models of Diamond Blackfan Anemia," 55 ASH Annual Meeting and Exposition. Abstract #3702 (2013).
Ferguson et al., "The role of effectors of the activin signalling pathway, activin receptors IIA and IIB, and Smad2, in patterning of tooth development," Development, vol. 128: 4605-4613 (2001).
Frankel et al., "Characterization of diphtheria fusion proteins targeted to the human interleukin-3 receptor," Protein Engineering, vol. 13(8): 575-581 (2000).
Kanemitsu, Fusae, "Clinical application of subforms of creatine kinase MM and macro creatine kinases," Journal of Chromatography, vol. 526: 423-438 (1990).
Kwiatkowski, J.L. et al., "Iron chelation therapy in sickle-cell disease and other transfusion-dependent anemias," Hematol Oncol Clin N Am., vol. 18: 1355-1377 (2004) (abstract).
MacLennan et al., "Multiple Myeloma," BMJ, vol. 308:1033-1036 (1994).
Marri et al, "Human Biochemistry, Moscow, Mir", vol. 1: 34-35 (1993).
Merck Manual. Iron-Utilization Anemias (Sideroblastic Anemias), pp. 1150-1151 (1992).
Merck Manual of Diagnosis and Therapy, 17th Edition. Nyelodysplastic Syndrome, pp. 865 and 963-955 (1999).
Moore et al., "Molecular Basis of Bone Morphogenetic Protein-15 Signaling in Granulosa Cells," The Journal of Biological Chemistry, vol. 278(1): 304-310 (2003).
Multiple Myeloma Research Foundation, themmrf.org/multiple-myeloma/symptoms/bone-lesions/, 2 pages total (downloaded from the website Oct. 28, 2014).

(56) References Cited

OTHER PUBLICATIONS

Nolan, V.G., et al, 'Sickle Cell Leg Ulcers: Associations with Haemolysis and SNPs in Klotho, TEK and Genes of the TGF-β/BMP Pathway:-Sickle Cell Leg Ulcers, Genetics and Haemolysis', British Journal of Haematology, 133(5), pp. 570-578 (2006).
Pak et al., "Suppression of hepcidin during anemia requires erythropoietic activity," Blood, vol. 108(12): 3730-3735 (2006).
Pakula and Sauer, "Genetic analysis of protein stability and function," Annu. Rev. Genet., vol. 23: 289-310 (1989).
Paulson, Robert F., "Targeting a new regulator of erythropoiesis to alleviate anemia," Nature Medicine, News and Views, vol. 20(4) (2 pages) (2014).
Sun Shuhan et al., "Chromosome, Gene, and Disesase," Science Press (2009).
Suragani et al., "Transforming growth factor-β superfamily ligand trap ACE-536 corrects anemia by promoting late-stage erythropoiesis," Letters, Nature Medicine, Advance Online Publication (44 pages) (2014).
US Biological Technical Data Sheet for A0856-10A, accessed on Feb. 20, 2013.
Ware, Russell E., "How I use hydroxyurea to treat young patients with sickle cell anemia," Blood, vol. 115(26): 5300-5311 (2010).

\* cited by examiner

```
  1  MDAMKRGLCC VLLLCGAVFV SPGAAETREC IYYNANWELE RTNQSGLERC
 51  EGEQDKRLHC YASWRNSSGT IELVKKGCWL DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 14)
```

FIGURE 13

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

A  E  T  R  E  C  I  Y  Y
 51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N  A  N  W  E  L  E  R  T  N  Q  S  G  L  E  R  C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E  G  E  Q  D  K  R  L  H  C  Y  A  S  W  R  N  S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S  G  T  I  E  L  V  K  K  G  W  L  D  D  F
201  CTCTGGCACC ATCGAGCTCG TGAAGAAGGG CTGCTGGCTA GATGACTTCA
     GAGACCGTGG TAGCTCGAGC ACTTCTTCCC GACGACCGAT CTACTGAAGT

N  C  Y  D  R  Q  E  C  V  A  T  E  E  N  P  Q  V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y  F  C  C  E  G  N  F  C  N  E  R  F  T  H  L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P  E  A  G  P  E  V  T  Y  E  P  P  P  T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
     CGTTCCAGAG GTTGTTTCGG GAGGGTCGGG GGTAGCTCTT TTGGTAGAGG
```

FIGURE 14

```
 751    AAAGCCAAAG GGCAGCCCCG AGAACCACAG GTGTACACCC TGCCCCCATC
        TTTCGGTTTC CCGTCGGGGC TCTTGGTGTC CACATGTGGG ACGGGGGTAG

801    CCGGGAGGAG ATGACCAAGA ACCAGGTCAG CCTGACCTGC CTGGTCAAAG
        GGCCCTCCTC TACTGGTTCT TGGTCCAGTC GGACTGGACG GACCAGTTTC

851    GCTTCTATCC CAGCGACATC GCCGTGGAGT GGGAGAGCAA TGGGCAGCCG
        CGAAGATAGG GTCGCTGTAG CGGCACCTCA CCCTCTCGTT ACCCGTCGGC

901    GAGAACAACT ACAAGACCAC GCCTCCCGTG CTGGACTCCG ACGGCTCCTT
        CTCTTGTTGA TGTTCTGGTG CGGAGGGCAC GACCTGAGGC TGCCGAGGAA

951    CTTCCTCTAT AGCAAGCTCA CCGTGGACAA GAGCAGGTGG CAGCAGGGGA
        GAAGGAGATA TCGTTCGAGT GGCACCTGTT CTCGTCCACC GTCGTCCCCT

1001    ACGTCTTCTC ATGCTCCGTG ATGCATGAGG CTCTGCACAA CCACTACACG
        TGCAGAAGAG TACGAGGCAC TACGTACTCC GAGACGTGTT GGTGATGTGC

1051    CAGAAGAGCC TCTCCCTGTC CCCGGGTAAA TGA (SEQ ID NO: 15)
        GTCTTCTCGG AGAGGGACAG GGGCCCATTT ACT (SEQ ID NO: 16)
```

FIGURE 14 CONT

METHODS FOR INCREASING THERMOGENIC ADIPOCYTES

CROSS-REFERENCE TO RELATED APPLICATIONS

This application is a continuation of U.S. application Ser. No. 13/403,657, filed Feb. 23, 2012, which is a continuation of U.S. application Ser. No. 12/796,332, filed Jun. 8, 2010 (now U.S. Pat. No. 8,178,488), which claims the benefit of U.S. Provisional Application Nos. 61/280,545, filed Nov. 3, 2009, 61/276,422, filed Sep. 10, 2009, and 61/268,128, filed Jun. 8, 2009. The specifications of each of the foregoing applications are incorporated herein by reference in their entirety.

SEQUENCE LISTING

The instant application contains a Sequence Listing which has been submitted via EFS-Web and is hereby incorporated by reference in its entirety. Said ASCII copy, created on Apr. 1, 2014, is named PHPH050103_Seq.txt, and is 35,228 bytes in size.

BACKGROUND OF THE INVENTION

Mammalian fat cells are traditionally classified as either energy-storing white adipocytes or energy-expending brown adipocytes. Brown adipocytes express uncoupling protein-1 (UCP1), which converts biochemical energy to heat by uncoupling ATP production from the mitochondrial proton gradient (Cannon et al., 2004, Physiol Rev 84:277-359). Such thermogenesis serves to maintain body temperature in cold environmental conditions or to promote energy balance in the face of excess caloric intake. Underscoring the metabolic importance of brown fat, its genetic ablation in mice results in severe obesity accompanied by insulin resistance, hyperglycemia, hyperlipidemia, and hypercholesterolemia (Lowell et al., 1993, Nature 366:740-742; Hamann et al., 1995, Diabetes 44:1266-1273; Hamann et al., 1996, Endocrinology 137:21-29). Given the role of UCP-1 as an important uncoupling protein, adipocytes that express UCP-1 will have a thermogenic activity.

In humans, brown adipose tissue plays an important thermogenic role in infants but shrinks during postnatal development and has historically been dismissed as sparse and clinically unimportant in adults. However, recent findings have overturned this thinking and generated considerable interest in the role(s) of brown adipose tissue during adulthood. Specifically, combined use of positron-emission tomography and computed tomography (PET-CT) to monitor tumor metastasis led to serendipidous detection of highly active, putative brown fat depots in a substantial percentage of adults (Nedergaard et al., 2007, Am J Physiol Endocrinol Metab 293:E444-E452). Subsequent studies have confirmed in healthy adults that these depots are indeed UCP1-expressing, functional brown fat (Virtanen et al., 2009, N Engl J Med 360:1518-1525), with brown-adipose-tissue activity observed during cold exposure but not thermoneutral conditions in more than 90% of young men studied (van Marken Lichtenbelt et al., 2009, N Engl J Med 360:1500-1508). Moreover, retrospective analysis of nearly two thousand PET-CT scans performed for various diagnostic reasons indicates that the amount of active brown fat is inversely correlated with body-mass index, a widely used measure of overall adiposity, raising the possibility of important beneficial roles for brown fat in adult human metabolism (Cypess et al., 2009, N Engl J Med 360:1509-1517). Less clear is the role of thermogenic adipocytes (e.g., brown adipocytes or other UCP-1 expressing adipocytes) that are interspersed with white adipose tissue.

Given the important metabolic activities of thermogenic adipocytes, there is a need for agents that increase (e.g., by formation and/or increased activity) thermogenic adipocytes in vivo.

SUMMARY OF THE INVENTION

In certain aspects, the present disclosure provides methods for increasing thermogenic adipocytes in patients by using antagonists of the ActRIIB signaling pathway. Such antagonists may be, for example, soluble ActRIIB proteins (e.g., ActRIIB-Fc fusion proteins), antagonists that bind to ActRIIB or inhibit ActRIIB expression, and antagonists that bind to or inhibit the expression of ligands that signal through ActRIIB and participate in the regulation of thermogenic adipocytes. Such ligands include myostatin (i.e., GDF8), GDF3, activins (e.g., activin A, B, C, or E), GDF11, and Nodal.

In certain aspects, the disclosure provides methods for increasing thermogenic adipocytes by administering to a patient in need thereof an effective amount of an ActRIIB-related polypeptide. An ActRIIB-related polypeptide may be an ActRIIB polypeptide (e.g., an ActRIIB extracellular domain or portion thereof) that binds to an ActRIIB ligand such as GDF3, GDF8, GDF11, activin or Nodal. Optionally, the ActRIIB polypeptide binds to an ActRIIB ligand with a Kd less than 10 micromolar or less than 1 micromolar, 100, 10 or 1 nanomolar. A variety of suitable ActRIIB polypeptides have been described in the following published PCT patent applications, all of which are incorporated by reference herein: WO 00/43781, WO 04/039948, WO 06/012627, WO 07/053775, WO 08/097541, and WO 08/109167. Optionally, the ActRIIB polypeptide inhibits ActRIIB signaling, such as intracellular signal transduction events triggered by an ActRIIB ligand. A soluble ActRIIB polypeptide for use in such a preparation may be any of those disclosed herein, such as a polypeptide having an amino acid sequence selected from SEQ ID NOs: 1, 2, 5, 6, 12, 14 and 17, or having an amino acid sequence that is at least 80%, 85%, 90%, 95%, 97% or 99% identical to an amino acid sequence selected from SEQ ID NOs: 1, 2, 5, 6, 12, 14 and 17. A soluble ActRIIB polypeptide may include a functional fragment of a natural ActRIIB polypeptide, such as one comprising at least 10, 20 or 30 amino acids of a sequence selected from SEQ ID NOs: 1, 2, 5, 6, 12, 14 and 17 or a sequence of SEQ ID NO: 1, lacking the C-terminal 1, 2, 3, 4, 5 or 10 to 15 amino acids and lacking 1, 2, 3, 4 or 5 amino acids at the N-terminus Optionally, polypeptides will comprise a truncation relative to SEQ ID NO:1 of between 2 and 5 amino acids at the N-terminus and no more than 3 amino acids at the C-terminus Another polypeptide is that presented as SEQ ID NO:12. A soluble ActRIIB polypeptide may include one, two, three, four, five or more alterations in the amino acid sequence (e.g., in the ligand-binding domain) relative to a naturally occurring ActRIIB polypeptide. The alteration in the amino acid sequence may, for example, alter glycosylation of the polypeptide when produced in a mammalian, insect or other eukaryotic cell or alter proteolytic cleavage of the polypeptide relative to the naturally occurring ActRIIB polypeptide. A soluble ActRIIB polypeptide may be a fusion protein that has, as one domain, an ActRIIB polypeptide (e.g., a ligand-binding domain of an ActRIIB or a variant thereof) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. A soluble ActRIIB fusion protein may include an immunoglobulin constant domain, such as an Fc domain (wild-type or mutant) or a serum albumin. In certain embodiments, an ActRIIB-Fc fusion comprises a relatively unstructured linker positioned between the Fc domain and the extracellular ActRIIB domain. This unstructured linker may correspond to the roughly 15 amino acid unstructured region at the C-terminal end of the extracellular domain of ActRIIB (the "tail"), or it may be an artificial sequence of between 5 and 15, 20, 30, 50 or more amino acids that are relatively free of secondary structure. A linker may be rich in glycine and proline residues and may, for example, contain repeating sequences of threonine/serine and glycines, e.g., $TG_4$ (SEQ ID NO: 18) or $SG_4$ repeats (SEQ ID NO: 19). A fusion protein may include a purification subsequence, such as an epitope tag, a FLAG tag, a polyhistidine sequence, and a GST fusion. Optionally, a soluble ActRIIB polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In general, it is preferable that an ActRIIB protein be expressed in a mammalian cell line that mediates suitably natural glycosylation of the ActRIIB protein so as to diminish the likelihood of an unfavorable immune response in a patient. Human and CHO cell lines have been used successfully, and it is expected that other common mammalian expression vectors will be useful.

In certain aspects, a compound disclosed herein may be formulated as a pharmaceutical preparation. A pharmaceutical preparation may also include one or more additional compounds such as a compound that is used to treat an ActRIIB-associated disorder. Preferably, a pharmaceutical preparation is substantially pyrogen free.

In certain aspects, the disclosure provides nucleic acids encoding a soluble ActRIIB polypeptide, which do not encode a complete ActRIIB polypeptide. An isolated polynucleotide may comprise a coding sequence for a soluble ActRIIB polypeptide, such as described above. For example, an isolated nucleic acid may include a sequence coding for an extracellular domain (e.g., ligand-binding domain) of an ActRIIB and a sequence that would code for part or all of the transmembrane domain and/or the cytoplasmic domain of an ActRIIB, but for a stop codon positioned within the transmembrane domain or the cytoplasmic domain, or positioned between the extracellular domain and the transmembrane domain or cytoplasmic domain. For example, an isolated polynucleotide may comprise a full-length ActRIIB polynucleotide sequence such as SEQ ID NO: 4, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRIIB. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a soluble ActRIIB polypeptide. Such a method may include expressing any of the nucleic acids (e.g., SEQ ID NO: 3) disclosed herein in a suitable cell, such as a Chinese hamster ovary (CHO) cell. Such a method may comprise: a) culturing a cell under conditions suitable for expression of the soluble ActRIIB polypeptide, wherein said cell is transformed with a soluble ActRIIB expression construct; and b) recovering the soluble ActRIIB polypeptide so expressed. Soluble ActRIIB polypeptides may be recovered as crude, partially purified or highly purified fractions using any of the well known techniques for obtaining protein from cell cultures.

In certain aspects, increasing thermogenic adipocytes using a compound described herein may be useful in the management of a variety of diseases in which management of metabolic activities is beneficial. Examples include management of obesity, decreasing the body fat content or reducing the rate of increase in body fat content, and treating a disorder such as obesity, non-insulin dependent diabetes mellitus (NIDDM), type 2 diabetes, cardiovascular disease, cancer, hypertension, stroke, respiratory problems, dyslipidemia, lipodystrophy, consequences of corticosteroid administration and gall bladder disease.

In certain aspects, a soluble ActRIIB polypeptide disclosed herein may be used in a method for treating a subject having a disorder associated with muscle loss or insufficient muscle growth wherein such disorder is also associated with a metabolic disorder, such as obesity, lipodystrophy, diabetes (e.g., type II diabetes), cachexia or other disorder described above. Such disorders include muscular dystrophy, sarcopenia and HIV (which may be associated with both a muscle wasting and a lipodystrophy).

In certain aspects, the disclosure provides methods for antagonizing activity of an ActRIIB polypeptide or an ActRIIB ligand (e.g., GDF8, GDF11, activin, GDF3, and Nodal) in a cell. The methods comprise contacting the cell with a soluble ActRIIB polypeptide. Optionally, the activity of the ActRIIB polypeptide or the ActRIIB ligand is monitored by a signaling transduction mediated by the ActRIIB/ActRIIB ligand complex, for example, by monitoring cell proliferation or the level of UCP-1 expression. The cells of the methods include an osteoblast, a chondrocyte, a myocyte, an adipocyte and a muscle cell.

In certain aspects, the disclosure provides uses of a soluble ActRIIB polypeptide for making a medicament for the treatment of a disorder or condition as described herein.

In certain aspects, the disclosure provides methods for increasing thermogenic adipocytes in a patient in need thereof, and such method may comprise administering an effective amount of a compound selected from the group consisting of: a polypeptide comprising an amino acid sequence that is at least 90% identical to the sequence of amino acids 29-109 of SEQ ID NO:2 and a polypeptide encoded by a nucleic acid that hybridizes under stringent hybridization conditions to a nucleic acid of SEQ ID NO:3. The polypeptide may be a fusion protein comprising a heterologous portion. The polypeptide may be a dimer. The polypeptide may be fused to a constant domain of an immunoglobulin. The polypeptide may be fused to an Fc portion of an immunoglobulin, such as an IgG1, IgG2, IgG3 or IgG4. The polypeptide may comprise an amino acid sequence that is at least 80%, 90%, 93%, 95%, 97%, 98%, 99% or 100% identical to the sequence of amino acids 29-109, 29-128, 29-131, 29-134, 25-109, 25-128, 25-131, 25-134 or 20-134 of SEQ ID NO:2. The polypeptide may comprise an amino acid sequence that is at least 80%, 90%, 93%, 95%, 97%, 98%, 99% or 100% identical to the sequence of amino acids of SEQ ID NO:5, 6, 12, 14 or 17. A patient to be treated with such a compound may one having a disorder described herein, including, for example, a metabolic disorder (e.g., obesity, diabetes, metabolic syndrome, dyslipidemia or lipodystrophy) or a muscle disorder that is associated with a metabolic disorder (e.g., some instances of sarcopenia). Administration of the compound may promotes UCP-1 expression in adipocytes of the treated patient, optionally in the white adipose tissue.

In certain aspects, the disclosure provides methods for increasing thermogenic adipocytes in a patient in need thereof, the method comprising administering an effective amount of a compound that inhibits the ActRIIB signaling pathway, either by targeting ActRIIB or a ligand that signals through ActRIIB. Examples of such compounds include antagonists of ActRIIB; antagonists of myostatin (i.e., GDF-8); antagonists of activin (e.g., activin A, activin B, activin C, or activin E); antagonists of GDF-11; antagonists of Nodal; and antagonists of GDF3. Antagonists of each of the foregoing may be an antibody or other protein that specifically binds to and inhibits such target (e.g., an antibody such as a monoclonal antibody, or a propeptide in the case of myostatin and GDF3). Antagonists of the foregoing may also be a compound, such as a nucleic acid based compound (e.g., an antisense or RNAi nucleic acid) that inhibits the expression of ActRIIB or the ligand. A patient to be treated with such a compound may one having a disorder described herein, including, for example, a metabolic disorder (e.g., obesity, diabetes, metabolic syndrome, dyslipidemia or lipodystrophy) or a muscle disorder that is associated with a metabolic disorder (e.g., some instances of sarcopenia). Administration of the compound may promotes UCP-1 expression in adipocytes of the treated patient, optionally in the white adipose tissue.

BRIEF DESCRIPTION OF THE DRAWINGS

The patent or application file contains at least one drawing executed in color. Copies of this patent or patent application publication with color drawing(s) will be provided by the Patent Office upon request and payment of the necessary fee.

FIG. 13 shows the full amino acid sequence of ActRIIB (25-131)-hFc (SEQ ID NO:14). The TPA leader (residues 1-22) and truncated ActRIIB extracellular domain (native residues 25-131) are each underlined. Highlighted is the glutamate revealed by sequencing to be the N-terminal amino acid of the mature fusion protein.

FIG. 14 shows a nucleotide sequence encoding ActRIIB (25-131)-hFc (the coding strand, SEQ ID NO: 15, is shown at top and the complement, SEQ ID NO: 16, is shown at bottom 3'-5'). Sequences encoding the TPA leader (nucleotides 1-66) and ActRIIB extracellular domain (nucleotides 73-396) are underlined. The corresponding amino acid sequence for ActRIIB(25-131) is also shown.

DETAILED DESCRIPTION

1. Overview

Figure 1:
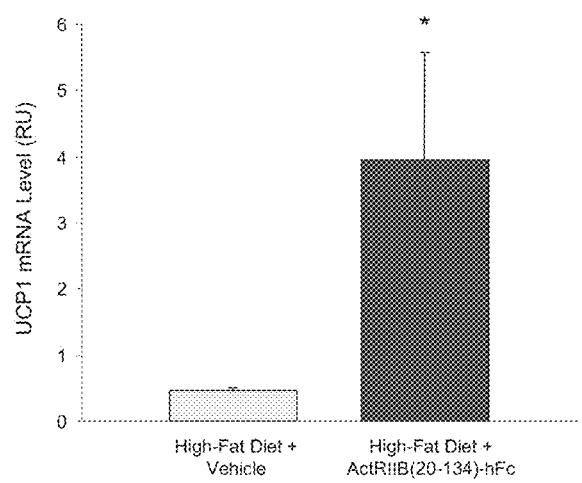
FIG. 1 shows the effect of ActRIIB(20-134)-hFc treatment for 60 days on uncoupling protein-1 (UCP1) mRNA levels in the epididymal fat pad of male mice fed a high-fat diet. RT-PCR data (in relative units, RU) are means±SEM; *, $p<0.05$ compared to vehicle. ActRIIB(20-134)-hFc caused a nearly nine-fold increase in mRNA encoding this selective marker for brown fat, thus indictating upregulation of thermogenic capability in brown adipocytes distributed diffusely within this white fat depot.

Mammalian fat cells can be classified as either energy-storing white adipocytes or energy-expending brown adipocytes. Uncoupling protein-1 (UCP1), which converts biochemical energy to heat by uncoupling ATP production from the mitochondrial proton gradient, is widely considered to be the definitive functional marker for brown adipocytes. Adipocytes expressing UCP-1 are referred to herein as "thermogenic adipocytes". Genetic ablation of brown adipose tissue in mice leads to extreme obesity (Lowell et al., 1993, Nature 366:740-742), and selective ablation of UCP1 prevents the thermogenic and anti-obesity responses to $\beta_3$-adrenergic stimulation in mice (Inokuma et al., 2006, Am J Physiol Endocrinol Metab 290:E1014-E1021), confirming that UCP1 is a critical molecule in the regulation of energy expenditure and adiposity (Kozak et al., 2008, Int J Obes 32:S32-S38).

In mammals ranging from rodents to humans, brown adipocytes occur in discrete depots of brown adipose tissue that are most prominent neonatally, consistent with the thermal challenges to survival at this age. Recent findings indicate that these brown fat depots persist with thermogenic capability during adulthood in humans (Nedergaard et al., 2007, Am J Physiol Endocrinol Metab 293:E444-E452; van Marken Lichtenbelt et al., 2009, N Engl J Med 360:1500-1508; Cypess et al., 2009, N Engl J Med 360:1509-1517), raising the possibility that such tissue might be activated exogenously for therapeutic benefit. Intriguingly, considerable numbers of brown adipocytes also occur transiently within some 'white' fat depots during early postnatal development (Xue et al., 2007, J Lipid Res 48:41-51) and can reappear in white fat depots under certain conditions in adulthood (Cousin et al., 1992, J Cell Sci 103:931-942). Even in humans, limited evidence suggests that brown adipocytes are inducible in white fat depots during adulthood (Lean et al., 1986, Int J Obes 10:219-227). Thus, there is also the possibility that 'diffuse' thermogenic adipocytes could be induced in traditional white fat depots for therapeutic benefit. Traditional depots of white adipose tissue, in fact, display a degree of cellular remodeling, or phenotypic plasticity, not observed in discrete brown fat depots (Prunet-Marcassus et al., 2006, Exp Cell Res 312:727-736).

As described in the Examples, an ActRIIB-Fc fusion protein can be used to increase UCP-1 signaling in fat depots of mice fed a high fat diet. Therefore, ActRIIB-derived agents and other compounds that inhibit ActRIIB signaling can be used to increase the number and/or activity of thermogenic adipocytes. Ligands that bind to ActRIIB which are implicated in the regulation of thermogenic adipocytes include the activins (e.g., activin A, activin B, activin C, and activin E), myostatin (i.e., GDF-8), GDF-3, GDF-11, and Nodal. In certain aspects, the present invention relates to ActRIIB polypeptides. As used herein, the term "ActRIIB" refers to a family of activin receptor type IIB (ActRIIB) proteins and ActRIIB-related proteins, derived from any species. Members of the ActRIIB family are generally all transmembrane proteins, composed of a ligand-binding extracellular domain with cysteine-rich region, a transmembrane domain, and a cytoplasmic domain with predicted serine/threonine kinase specificity. The human ActRIIB precursor has the following amino acid sequence, with the signal peptide underlined, the extracellular domain indicated in bold, and the potential N-linked glycosylation sites boxed (SEQ ID NO: 2) (NM 001106, 512 aa).

---

MTAPWVALALLWGSLWPSSGRGEAETRECIYYNANWELERTNQSGLER

CEGEQDKRLHCYASWRNSSGTIELVKKGCWLDDFNCYDRQECVATEEN

PQVYFCCCEGNFCNERFTHLPEAGGPEVTYEPPPTAPTLLTVLAYSLL

PIGGLSLIVLLAFWMYRHRKPPYGHVDIHEDPGPPPPSPLVGLKPLQL

LEIKARGRFGCVWKAQLMNDFVAVKIFPLQDKQSWQSEREIFSTPGMK

HENLLQFIAAEKRGSNLEVELWLITAFHDKGSLTDYLKGNIITWNELC

HVAETMSRGLSYLHEDVPWCRGEGHKPSIAHRDFKSKNVLLKSDLTAV

LADFGLAVRFEPGKPPGDTHGQVGTRRYMAPEVLEGAINFQRDAFLRI

DMYAMGLVLWELVSRCKAADGPVDEYMLPFEEEIGQHPSLEELQEVVV

HKKMRPTIKDHWLKHPGLAQLCVTIEECWDHDAEARLSAGCVEERVSL

IRRSVNGTTSDCLVSLVTSVTNVDLPPKESSI

---

The above wild type sequence, including the native leader, is used throughout this disclosure as the base sequence for numbering the amino acids of any of the various truncations, mature forms and variants of ActRIIB. The term "ActRIIB polypeptide" is used to refer to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB having a sequence at least about 80% identical to the sequence of an ActRIIB polypeptide, and preferably at least 85%, 90%, 95%, 97%, 99% or greater identity.

In a specific embodiment, the invention relates to soluble ActRIIB polypeptides. As described herein, the term "soluble ActRIIB polypeptide" generally refers to polypeptides comprising an extracellular domain of an ActRIIB protein. The term "soluble ActRIIB polypeptide," as used herein, includes any naturally occurring extracellular domain of an ActRIIB protein as well as any variants thereof (including mutants, fragments and peptidomimetic forms) that retain a useful activity. For example, the extracellular domain of an ActRIIB protein binds to a ligand and is generally soluble. The following is an example of a soluble ActRIIB polypeptide (SEQ ID NO: 1) (116 aa).

```
SGRGEAETRECIYYNANWELERTNQSGLERCEGEQDKRLHCYAS

WRNSSGTIELVKKGCWLDDFNCYDRQECVATEENPQVYFCCCEG

NFCNERFTHLPEAGGPEVTYEPPPTAPT
```

Other examples of soluble ActRIIB polypeptides comprise a signal sequence in addition to the extracellular domain of an ActRIIB protein (see Example 1). The signal sequence can be a native signal sequence of an ActRIIB, or a signal sequence from another protein, such as a tissue plasminogen activator (TPA) signal sequence or a honey bee mellitin (HBM) signal sequence.

Two related type II receptors, ActRIIA and ActRIIB, have been identified as the type II receptors for activins (Mathews and Vale, 1991, Cell 65:973-982; Attisano et al., 1992, Cell 68: 97-108) as well as a variety of other BMPs and GDFs. Besides activins, ActRIIA and ActRIIB can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). In certain embodiments, the present invention relates to antagonizing a ligand of ActRIIB receptors (also referred to as an ActRIIB ligand) with a subject ActRIIB polypeptide (e.g., a soluble ActRIIB polypeptide). Thus, compositions and methods of the present invention are useful for treating disorders associated with abnormal activity of one or more ligands of ActRIIB receptors. Exemplary ligands of ActRIIB receptors include some TGF-β family members, such as activin (e.g., activin A, activin B, activin C, and activin E), GDF3, Nodal, GDF8, and GDF11.

Activins are dimeric polypeptide growth factors and belong to the TGF-beta superfamily. There are three activins (A, B, and AB) that are homo/heterodimers of two closely related β subunits ($β_Aβ_A$, $β_Bβ_B$, and $β_Aβ_B$). In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc SocEp Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It was suggested that activin A acts as a natural regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $α_2$-macroglobulin, Cerberus, and endoglin, which are described below.

Bone morphogenetic protein 7 (BMP7), also called osteogenic protein-1 (OP-1), is well known to induce cartilage and bone formation. In addition, BMP7 regulates a wide array of physiological processes. Notably, BMP7 has recently been identified as a key promoter of brown adipocyte differentiation (Tseng et al., 2008, Nature 454:1000-1004). In this study, genetic ablation of BMP7 led to scarcity of brown fat and nearly complete absence of UCP1 in murine embryos. Moreover, upregulation of BMP7 expression in mice by adenovirus administration increased brown fat mass and energy expenditure. Therefore, the literature would suggest that an antagonist of BMP7 such as an ActRIIB polypeptide or anti-ActRIIB antibody would not be expected to promote UCP 1 expression, brown adipocyte formation, and/or brown adipocyte activity. Like activin, BMP7 binds to type II receptors, ActRIIA and ActRIIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different Smad pathways (Macias-Silva et al., 1998, J Biol Chem. 273:25628-36).

Growth-and-Differentiation Factor-3 (GDF3), also known as Vg1-related 2, plays an important role in embryonic development and has also been implicated in adipogenesis during adulthood. In brief, expression of GDF3 in white adipose tissue is correlated with body mass or obesity (Weisberg et al., 2003, J Clin Invest 112:1796-1808), and adenovirus-mediated overexpression of GDF3 exaggerates the increase in adiposity observed under high-fat dietary conditions in wildtype mice (Wang et al., 2004, Biochem Biophys Res Commun 321:1024-1031). Importantly, mice with genetic ablation of GDF3 are healthy and essentially normal when maintained on a standard diet but are protected from obesity, and display an increased basal metabolic rate, when maintained on a high-fat diet (Shen et al., 2009, Mol Endocrinol 23:113-123). Taken together, these findings implicate GDF3 specifically in diet-induced obesity and more generally in the regulation of adiposity.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as Smad proteins. Recent studies support the idea that ActRIIA and ActRIIB serve as type II receptors for Nodal (Sakuma et al., Genes Cells. 2002, 7:401-12). It is suggested that Nodal ligands interact with their co-factors (e.g., cripto) to activate activin type I and type II receptors, which phosphorylate Smad2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pT1x2-Lux, a reporter specifically responsive to bone morphogenetic proteins. Recent results provide direct biochemical evidence that Nodal signaling is mediated by both activin-TGF-beta pathway Smads, Smad2 and Smad3. Further evidence has shown that the extracellular cripto protein is required for Nodal signaling, making it distinct from activin or TGF-beta signaling.

Growth and Differentiation Factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim. Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (1999) Dev. Biol., 208: 222-232).

Growth and Differentiation Factor-11 (GDF11), also known as BMP11, is a secreted protein (McPherson et al., 1999, Nat. Genet. 22: 260-264). GDF11 is expressed in the tail bud, limb bud, maxillary and mandibular arches, and dorsal root ganglia during mouse development (Nakashima et al., 1999, Mech. Dev. 80: 185-189). GDF11 plays a unique role in patterning both mesodermal and neural tissues (Gamer et al., 1999, Dev Biol., 208:222-32). GDF11 was shown to be a negative regulator of chondrogenesis and myogenesis in developing chick limb (Gamer et al., 2001, Dev Biol. 229:407-20). The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF 11 was found to inhibit neurogenesis in the olfactory epithelium (Wu et al., 2003, Neuron. 37:197-207). Hence, GDF11 may have in vitro and in vivo applications in the treatment of diseases such as muscle diseases and neurodegenerative diseases (e.g., amyotrophic lateral sclerosis).

In certain aspects, the present invention relates to the use of certain ActRIIB polypeptides (e.g., soluble ActRIIB polypeptides) to antagonize the signaling of ActRIIB ligands generally, in any process associated with ActRIIB activity. Optionally, ActRIIB polypeptides of the invention may antagonize one or more ligands of ActRIIB receptors, such as activin (e.g., activin A, activin B, activin C, and activin E), GDF3, Nodal, GDF8, and GDF11, and may therefore be useful in the treatment of additional disorders.

Therefore, the present disclosure contemplates using ActRIIB polypeptides and antagonists of ActRIIB or ActRIIB ligands in treating or preventing diseases or conditions that are related to the activities of thermogenic adipocytes. ActRIIB or ActRIIB ligands are involved in the regulation of many critical biological processes. Examples of such metabolic disorders or conditions include, but are not limited to, metabolic syndrome (also known as syndrome X), diabetes, impaired glucose tolerance, impaired fasting glucose, elevated plasma insulin concentrations and insulin resistance, dyslipidemias, hyperlipidemia, overeating and bulimia, cancers of the colon, prostate, breast, endometrium, and kidney, osteoarthritis, obstructive sleep apnea, cholelithiasis, gallstones, hypertension, heart disease, abnormal heart rhythms and arrythmias, myocardial infarction, congestive heart failure, coronary heart disease, coronary artery disease, angina pectoris, sudden death, polycystic ovarian disease, craniopharyngioma, the Prader-Willi syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples are sexual and reproductive dysfunction (such as infertility), hypogonadism in males and hirsutism in females, gastrointestinal motility disorders (such as obesity-related gastro-esophageal reflux, respiratory disorders (such as obesity-hypoventilation syndrome or Pickwickian syndrome), cardiovascular disorders, cerebral infarction, cerebral thrombosis, transient ischemic attack, inflammation (such as systemic inflammation of the vasculature), arteriosclerosis, hypercholesterolemia, hyperuricacidemia, fatty liver, gout, gallbladder disease, orthopedic disorders, and lower back pain. These disorders and conditions are discussed below under "Exemplary Therapeutic Uses."

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

The term "diabetes", as used herein, refers to non-insulin-dependent diabetes mellitus (NIDDM, also known as type II diabetes). Type I diabetes, or insulin-dependent diabetes mellitus (IDDM), is the result of an absolute deficiency of insulin, the hormone which regulates glucose utilization. Type II diabetes, or insulin-dependent diabetes (i.e., non-insulin-dependent diabetes mellitus), often occurs in the face of normal, or even elevated, levels of insulin and appears to be the result of the inability of tissues to respond appropriately to insulin. Most type II diabetics are also obese.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

"Obesity" is a condition in which there is an excess of body fat. The operational definition of obesity is based on the body mass index (BMI), calculated as body weight per height in meters squared ($kg/m^2$). "Obesity" refers to a condition that is diagnosed as such by a physician. One standard grading system is described as follows for patients of generally European, African, Native American or Indian descent, and an alternative system is often used for Asian patients. According to this system, obesity is defined as an otherwise healthy subject that has a BMI greater than or equal to 30 $kg/m^2$, or a condition whereby a subject with at least one co-morbidity has a BMI greater than or equal to 27 $kg/m^2$.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ActRIIB Polypeptides

In certain aspects, the invention relates to ActRIIB variant polypeptides (e.g., soluble ActRIIB polypeptides). Optionally, the fragments, functional variants, and modified forms have similar or the same biological activities of their corresponding wild-type ActRIIB polypeptides. For example, an ActRIIB variant of the invention may bind to and inhibit function of an ActRIIB ligand (e.g., activin A, activin AB, activin B, activin C, activin E GDF3, Nodal, GDF8, or GDF11). Optionally, an ActRIIB polypeptide modulates growth of tissues such as fat, muscle, bone, or cartilage. Examples of ActRIIB polypeptides include human ActRIIB precursor polypeptide (SEQ ID NO: 2), and soluble human ActRIIB polypeptides (e.g., SEQ ID NOs: 1, 5, 6, 12, 14, and 17).

The disclosure identifies functionally active portions and variants of ActRIIB. Applicants have ascertained that an Fc fusion protein having the sequence disclosed by Hilden et al. (Blood. 1994 Apr. 15; 83(8):2163-70), which has an Alanine at the position corresponding to amino acid 64 of SEQ ID NO: 2 (A64), has a relatively low affinity for activin and GDF-11. By contrast, the same Fc fusion protein with an Arginine at position 64 (R64) has an affinity for activin and GDF-11 in the low nanomolar to high picomolar range. Therefore, a sequence with an R64 is used as the wild-type reference sequence for human ActRIIB in this disclosure.

Attisano et al. (Cell. 1992 Jan. 10; 68(1):97-108) showed that a deletion of the proline knot at the C-terminus of the extracellular domain of ActRIIB reduced the affinity of the receptor for activin. An ActRIIB-Fc fusion protein containing amino acids 20-119 of SEQ ID NO:2, "ActRIIB(20-119)-Fc" has reduced binding to GDF-11 and activin relative to an ActRIIB(20-134)-Fc, which includes the proline knot region and the complete juxtamembrane domain. However, an ActRIIB(20-129)-Fc protein retains similar but somewhat reduced activity relative to the wild type, even though the proline knot region is disrupted. Thus, ActRIIB extracellular domains that stop at amino acid 134, 133, 132, 131, 130 and 129 are all expected to be active, but constructs stopping at 134 or 133 may be most active. Similarly, mutations at any of residues 129-134 are not expected to alter ligand binding affinity by large margins. In support of this, mutations of P129 and P130 do not substantially decrease ligand binding. Therefore, an ActRIIB-Fc fusion protein may end as early as amino acid 109 (the final cysteine), however, forms ending at or between 109 and 119 are expected to have reduced ligand binding. Amino acid 119 is poorly conserved and so is readily altered or truncated. Forms ending at 128 or later retain ligand binding activity. Forms ending at or between 119 and 127 will have an intermediate binding ability. Any of these forms may be desirable to use, depending on the clinical or experimental setting.

At the N-terminus of ActRIIB, it is expected that a protein beginning at amino acid 29 or before will retain ligand binding activity. Amino acid 29 represents the initial cysteine. An alanine to asparagine mutation at position 24 introduces an N-linked glycosylation sequence without substantially affecting ligand binding. This confirms that mutations in the region between the signal cleavage peptide and the cysteine cross-linked region, corresponding to amino acids 20-29 are well tolerated. In particular, constructs beginning at position 20, 21, 22, 23 and 24 will retain activity, and constructs beginning at positions 25, 26, 27, 28 and 29 are also expected to retain activity.

Taken together, an active portion of ActRIIB comprises amino acids 29-109 of SEQ ID NO:2, and constructs may, for example, begin at a residue corresponding to amino acids 20-29 and end at a position corresponding to amino acids 109-134. Other examples include constructs that begin at a position from 20-29 or 21-29 and end at a position from 119-134, 119-133 or 129-134, 129-133. Other examples include constructs that begin at a position from 20-24 (or 21-24, or 22-25) and end at a position from 109-134 (or 109-133), 119-134 (or 119-133) or 129-134 (or 129-133). Variants within these ranges are also contemplated, particularly those having at least 80%, 85%, 90%, 95% or 99% identity to the corresponding portion of SEQ ID NO:2.

The disclosure includes the results of an analysis of composite ActRIIB structures demonstrating that the ligand binding pocket is defined by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, a general formula for an active ActRIIB variant protein is one that comprises amino acids 29-109, but optionally beginning at a position ranging from 20-24 or 22-25 and ending at a position ranging from 129-134, and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may retain greater than 80%, 90%, 95% or 99% sequence identity to the sequence of amino acids 29-109 of SEQ ID NO:2. Sites outside the binding pocket, at which variability may be particularly well tolerated, include the amino and carboxy termini of the extracellular domain (as noted above), and positions 42-46 and 65-73. An asparagine to alanine alteration at position 65 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

ActRIIB is well-conserved across nearly all vertebrates, with large stretches of the extracellular domain conserved completely. Many of the ligands that bind to ActRIIB are also highly conserved. Accordingly, comparisons of ActRIIB sequences from various vertebrate organisms provide insights into residues that may be altered. Therefore, an active, human ActRIIB variant may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in *Xenopus* ActRIIB, and so this position may be altered, and optionally may be altered to another hydrophobic residue, such as V, I or F, or a non-polar residue such as A. E52 is a K in *Xenopus*, indicating that this site may be tolerant of a wide variety of changes, including polar residues, such as E, D, K, R, H, S, T, P, G, Y and probably A. T93 is a K in *Xenopus*, indicating that a wide structural variation is tolerated at this position, with polar residues favored, such as S, K, R, E, D, H, G, P, G and Y. F108 is a Y in *Xenopus*, and therefore Y or other hydrophobic group, such as I, V or L should be tolerated. E111 is K in *Xenopus*, indicating that charged residues will be tolerated at this position, including D, R, K and H, as well as Q and N. R112 is K in *Xenopus*, indicating that basic residues are tolerated at this position, including R and H. A at position 119 is relatively poorly conserved, and appears as P in rodents and V in *Xenopus*, thus essentially any amino acid should be tolerated at this position.

The disclosure demonstrates that the addition of a further N-linked glycosylation site (N-X-S/T) increases the serum half-life of an ActRIIB-Fc fusion protein, relative to the ActRIIB(R64)-Fc form. By introducing an asparagine at position 24 (A24N construct), an NXT sequence is created that confers a longer half-life. Other NX(T/S) sequences are found at 42-44 (NQS) and 65-67 (NSS), although the latter may not be efficiently glycosylated with the R at position 64. N-X-S/T sequences may be generally introduced at positions outside the ligand binding pocket. Particularly suitable sites for the introduction of non-endogenous N-X-S/T sequences include amino acids 20-29, 20-24, 22-25, 109-134, 120-134 or 129-134. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T. Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are contemplated. Likewise, in an A24N variant, an S26T alteration may be used. Accordingly, an ActRIIB variant may include one or more additional, non-endogenous N-linked glycosylation consensus sequences.

Position L79 may be altered to confer altered activin-myostatin (GDF-11) binding properties. L79A or L79P reduces GDF-11 binding to a greater extent than activin binding. L79E or L79D retains GDF-11 binding. Remarkably, the L79E and L79D variants have greatly reduced activin binding. In vivo experiments indicate that these non-activin receptors retain significant ability to increase muscle mass but show decreased effects on other tissues. These data demonstrate the desirability and feasibility for obtaining polypeptides with reduced effects on activin.

The variations described may be combined in various ways. Additionally, the results of mutagenesis program described herein indicate that there are amino acid positions in ActRIIb that are often beneficial to conserve. These include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, in each of the variants disclosed herein, the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K).

In certain embodiments, isolated fragments of the ActRIIB polypeptides can be obtained by screening polypeptides recombinantly produced from the corresponding fragment of the nucleic acid encoding an ActRIIB polypeptide (e.g., SEQ ID NOs: 3 and 4). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of an ActRIIB protein or an ActRIIB ligand.

In certain embodiments, a functional variant of the ActRIIB polypeptides has an amino acid sequence that is at least 75% identical to an amino acid sequence selected from SEQ ID NOs: 1, 2, 5, 6, 12, 14, and 17. In certain cases, the functional variant has an amino acid sequence at least 80%, 85%, 90%, 95%, 97%, 98%, 99% or 100% identical to an amino acid sequence selected from SEQ ID NOs: 1, 2, 5, 6, 12, 14, and 17.

In certain embodiments, the present invention contemplates making functional variants by modifying the structure of an ActRIIB polypeptide for such purposes as enhancing therapeutic efficacy, or stability (e.g., ex vivo shelf life and resistance to proteolytic degradation in vivo). Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wild-type ActRIIB polypeptide, or to bind to one or more ligands, such as activin (e.g., activin A, activin B, activin C, and activin E), Nodal, GDF3, GDF-11, or myostatin in a fashion similar to wild type.

In certain embodiments, the present invention contemplates specific mutations of the ActRIIB polypeptides so as to alter the glycosylation of the polypeptide. Exemplary glycosylation sites in ActRIIB polypeptides are illustrated in SEQ ID NO: 2. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of an ActRIIB polypeptide, including, optionally, truncation variants; pools of combinatorial mutants are especially useful for identifying functional variant sequences. The purpose of screening such combinatorial libraries may be to generate, for example, ActRIIB polypeptide variants which have altered properties, such as altered pharmacokinetics, or altered ligand binding. A variety of screening assays are provided below, and such assays may be used to evaluate variants. For example, an ActRIIB polypeptide variant may be screened for ability to bind to an ActRIIB polypeptide, to prevent binding of an ActRIIB ligand to an ActRIIB polypeptide.

The activity of an ActRIIB polypeptide or its variants may also be tested in a cell-based or in vivo assay. For example, the effect of an ActRIIB polypeptide variant on the expression of genes involved in adipocyte differentiation or function may be assessed (e.g., UCP-1). This may, as needed, be performed in the presence of one or more recombinant ActRIIB ligand protein (e.g., GDF8), and cells may be transfected so as to produce an ActRIIB polypeptide and/or variants thereof, and optionally, an ActRIIB ligand. Likewise, an ActRIIB polypeptide may be administered to a mouse or other animal, and one or more properties of adipocytes, such as brown adipocyte thermogenesis may be assessed. Similarly, the activity of an ActRIIB polypeptide or its variants may be tested in fat cells, muscle cells, bone cells, and neuronal cells for any effect on growth of these cells, for example, by the assays as described below. Such assays are well known and routine in the art. A SMAD-responsive reporter gene may be used in such cell lines to monitor effects on downstream signaling.

Combinatorially-derived variants can be generated which have a selective potency relative to a naturally occurring ActRIIB polypeptide. Such variant proteins, when expressed from recombinant DNA constructs, can be used in gene therapy protocols. Likewise, mutagenesis can give rise to variants which have intracellular half-lives dramatically different than the corresponding a wild-type ActRIIB polypeptide. For example, the altered protein can be rendered either more stable or less stable to proteolytic degradation or other processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and, when part of an inducible expression system, can allow tighter control of recombinant ActRIIB polypeptide levels within the cell.

In certain embodiments, the ActRIIB polypeptides of the invention may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or mono-saccharide, and phosphates. Effects of such non-amino acid elements on the functionality of a ActRIIB polypeptide may be tested as described herein for other ActRIIB polypeptide variants. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

As a specific example, the present invention provides a fusion protein as a GDF8 antagonist which comprises an extracellular (e.g., GDF8-binding) domain fused to an Fc domain (e.g., SEQ ID NO: 13).

```
THTCPPCPAPELLGGPSVFLFPPKPKDTLMISRTPEVTCVVVD(A)

VSHEDPEVKFNWYVDGVEVHNAKTKPREEQYNSTYRVVSVLTVLHQ

DWLNGKEYKCK(A)VSNKALPVPIEKTISKAKGQPREPQVYTLPPS

REEMTKNQVSLTCLVKGFYPSDIAVEWESNGQPENNYKTTPPVLDS

DGPFFLYSKLTVDKSRWQQGNVFSCSVMHEALHN(A)HYTQKSLSL

SPGK
```

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ActRIIB polypeptide may be placed C-terminal to a heterologous domain, or, alternatively, a heterologous domain may be placed C-terminal to an ActRIIB polypeptide. The ActRIIB polypeptide domain and the heterologous domain need not be adjacent in a fusion protein, and additional domains or amino acid sequences may be included C- or N-terminal to either domain or between the domains.

In certain embodiments, the ActRIIB polypeptides of the present invention contain one or more modifications that are capable of stabilizing the ActRIIB polypeptides. For example, such modifications enhance the in vitro half life of the ActRIIB polypeptides, enhance circulatory half life of the ActRIIB polypeptides or reducing proteolytic degradation of the ActRIIB polypeptides. Such stabilizing modifications include, but are not limited to, fusion proteins (including, for example, fusion proteins comprising an ActRIIB polypeptide and a stabilizer domain), modifications of a glycosylation site (including, for example, addition of a glycosylation site to an ActRIIB polypeptide), and modifications of carbohydrate moiety (including, for example, removal of carbohydrate moieties from an ActRIIB polypeptide). In the case of fusion proteins, an ActRIIB polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the ActRIIB polypeptides, which are isolated from, or otherwise substantially free of, other proteins.

In certain embodiments, ActRIIB polypeptides (unmodified or modified) of the invention can be produced by a variety of art-known techniques. For example, such ActRIIB polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the ActRIIB polypeptides, fragments or variants thereof may be recombinantly produced using various expression systems (e.g., *E. coli*, Chinese Hamster Ovary cells, COS cells, baculovirus) as is well known in the art (also see below). In a further embodiment, the modified or unmodified ActRIIB polypeptides may be produced by digestion of naturally occurring or recombinantly produced full-length ActRIIB polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such ActRIIB polypeptides may be produced from naturally occurring or recombinantly produced full-length ActRIIB polypeptides such as standard techniques known in the art, such as by chemical cleavage (e.g., cyanogen bromide, hydroxylamine).

3. Nucleic Acids Encoding ActRIIB Polypeptides

In certain aspects, the invention provides isolated and/or recombinant nucleic acids encoding any of the ActRIIB polypeptides (e.g., soluble ActRIIB polypeptides), including any of the variants disclosed herein. For example, the following sequence encodes a naturally occurring human ActRIIB precursor polypeptide (SEQ ID NO: 4) (nucleotides 5-1543 of NM_001106, 1539 bp):

```
atgacggcgccctgggtggccctcgccctcctctggggatcgctgt
ggcccggctctgggcgtggggaggctgagacacgggagtgcatcta
ctacaacgccaactgggagctggagcgcaccaaccagagcggcctg
gagcgctgcgaaggcgagcaggacaagcggctgcactgctacgcct
cctggcgcaacagctctggcaccatcgagctcgtgaagaagggctg
ctggctagatgacttcaactgctacgataggcaggagtgtgtggcc
actgaggagaaccccaggtgtacttctgctgctgtgaaggcaact
tctgcaacgagcgcttcactcatttgccagaggctggggggcccgga
agtcacgtacgagccaccccgacagcccccaccctgctcacggtg
ctggcctactcactgctgcccatcgggggcctttccctcatcgtcc
tgctggccttttggatgtaccggcatcgcaagcccccctacggtca
tgtggacatccatgaggaccctgggcctccaccaccatcccctctg
gtgggcctgaagccactgcagctgctggagatcaaggctcggggc
gctttggctgtgtctggaaggcccagctcatgaatgactttgtagc
tgtcaagatcttcccactccaggacaagcagtcgtggcagagtgaa
cgggagatcttcagcacacctggcatgaagcacgagaacctgctac
agttcattgctgccgagaagcgaggctccaacctcgaagtagagct
gtggctcatcacggccttccatgacaagggctccctcacggattac
ctcaaggggaacatcatcacatggaacgaactgtgtcatgtagcag
agacgatgtcacgaggcctctcatacctgcatgaggatgtgccctg
gtgccgtggcgagggccacaagccgtctattgcccacagggacttt
aaaagtaagaatgtattgctgaagagcgacctcacagccgtgctgg
ctgactttggcttggctgttcgatttgagccagggaaacctccagg
ggacacccacggacaggtaggcacgagacggtacatggctcctgag
gtgctcgagggagccatcaacttccagagagatgccttcctgcgca
ttgacatgtatgccatggggttggtgctgtgggagcttgtgtctcg
ctgcaaggctgcagacggaccgtggatgagtacatgctgccctt
gaggaagagattggccagcacccttcgttggaggagctgcaggagg
tggtggtgcacaagaagatgaggcccaccattaaagatcactggtt
gaaacacccgggcctggcccagctttgtgtgaccatcgaggagtgc
tgggaccatgatgcagaggctcgcttgtccgcgggctgtgtggagg
agcgggtgtccctgattcggaggtcggtcaacggcactacctcgga
ctgtctcgtttccctggtgacctctgtcaccaatgtggacctgccc
cctaaagagtcaagcatctaa
```

The following sequence encodes a human soluble (extracellular) ActRIIB polypeptide (SEQ ID NO: 3) (348 bp).

```
tctgggcgtggggaggctgagacacgggagtgcatctactacaacgcc
aactgggagctggagcgcaccaaccagagcggcctggagcgctgcgaa
```

-continued
```
ggcgagcaggacaagcggctgcactgctacgcctcctggcgcaacagc
tctggcaccatcgagctcgtgaagaagggctgctggctagatgacttc
aactgctacgataggcaggagtgtgtggccactgaggagaacccccag
gtgtacttctgctgctgtgaaggcaacttctgcaacgagcgcttcact
catttgccagaggctgggggcccggaagtcacgtacgagccaccccg
acagccccacc
```

The subject nucleic acids may be single-stranded or double stranded. Such nucleic acids may be DNA or RNA molecules. These nucleic acids are may be used, for example, in methods for making ActRIIB polypeptides or as direct therapeutic agents (e.g., in a gene therapy approach).

In certain aspects, the subject nucleic acids encoding ActRIIB polypeptides are further understood to include nucleic acids that are variants of SEQ ID NO: 3. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 4.

In certain embodiments, the invention provides isolated or recombinant nucleic acid sequences that are at least 80%, 85%, 90%, 95%, 97%, 98%, 99% or 100% identical to SEQ ID NO: 3. One of ordinary skill in the art will appreciate that nucleic acid sequences complementary to SEQ ID NO: 3, and variants of SEQ ID NO: 3 are also within the scope of this invention. In further embodiments, the nucleic acid sequences of the invention can be isolated, recombinant, and/or fused with a heterologous nucleotide sequence, or in a DNA library. For example, the invention provides isolated or recombinant nucleic acid sequences that are at least 80%, 85%, 90%, 95%, 97%, 98%, 99% or 100% identical to SEQ ID NO: 10 or 15.

In other embodiments, nucleic acids of the invention also include nucleotide sequences that hybridize under highly stringent conditions to the nucleotide sequence designated in SEQ ID NO: 3, complement sequence of SEQ ID NO: 3, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NO: 3 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIB polypeptide and operably linked to at least one regulatory sequence. Regulatory sequences are art-recognized and are selected to direct expression of the ActRIIB polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIB polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 3, 4, 10, or 15) for one or more of the subject ActRIIB polypeptide. The host cell may be any prokaryotic or eukaryotic cell. For example, an ActRIIB polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject ActRIIB polypeptides. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the ActRIIB polypeptides. In a preferred embodiment, the ActRIIB polypeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant ActRIIB polypeptide, can allow purification of the expressed fusion protein by affinity chromatography using a $Ni^{2+}$ metal resin. The purification leader sequence can then be subsequently removed by treatment with enterokinase to provide the purified ActRIIB polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Antibodies and Other Antagonists

Another aspect of the invention pertains to antibodies and other antagonists, including proteins that bind to the targets disclosed herein and nucleic acids that inhibit expression of targets disclosed herein. An antibody that is specifically reactive with an ActRIIB polypeptide (e.g., a soluble ActRIIB polypeptide) and which binds competitively with the ActRIIB polypeptide may be used as an antagonist of ActRIIB polypeptide activities. For example, by using immunogens derived from an ActRIIB polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRIIB polypeptide or ligand, an antigenic fragment which is capable of eliciting an antibody response, or a fusion protein. Techniques for conferring immunogenicity on a protein or peptide include conjugation to carriers or other techniques well known in the art. An immunogenic portion of an ActRIIB polypeptide or ligand can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRIIB polypeptide or ligand, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, 1975, Nature, 256: 495-497), the human B cell hybridoma technique (Kozbar et al., 1983, Immunology Today, 4:72), and the EBV-hybridoma technique to produce human monoclonal antibodies (Cole et al., 1985, Monoclonal Antibodies and Cancer Therapy, Alan R. Liss, Inc. pp. 77-96). Hybridoma cells can be screened immunochemically for production of antibodies specifically reactive with an ActRIIB polypeptide and monoclonal antibodies isolated from a culture comprising such hybridoma cells.

The term "antibody" as used herein is intended to include fragments thereof which are also specifically reactive with a subject ActRIIB polypeptide or ligand. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an ActRIIB polypeptide conferred by at least one CDR region of the antibody. In preferred embodiments, the antibody further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments, the invention makes available methods for generating novel antibodies. For example, a method for generating a monoclonal antibody that binds specifically to an ActRIIB polypeptide or ligand may comprise administering to a mouse an amount of an immunogenic composition comprising the ActRIIB polypeptide or ligand effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the ActRIIB polypeptide or ligand. Once obtained, a hybridoma can be propagated in a cell culture, optionally in culture conditions where the hybridoma-derived cells produce the monoclonal antibody that binds specifically to the ActRIIB polypeptide or ligand. The monoclonal antibody may be purified from th e cell culture.

The adjective "specifically reactive with" as used in reference to an antibody is intended to mean, as is generally understood in the art, that the antibody is sufficiently selective between the antigen of interest (e.g., an ActRIIB polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

In certain aspects, the disclosure provides antibodies that bind to a soluble ActRIIB polypeptide or ligand. Such antibodies may be generated much as described above, using a soluble ActRIIB polypeptide or ligand or fragment thereof as an antigen. Antibodies of this type can be used, e.g., to detect ActRIIB polypeptides in biological samples and/or to monitor soluble ActRIIB polypeptide levels in an individual. In certain cases, an antibody that specifically binds to a soluble ActRIIB polypeptide or ligand can be used to modulate activity of an ActRIIB polypeptide and/or an ActRIIB ligand, thereby increasing thermogenic adipocytes.

Certain ligands, such as myostatin and GDF3 may be inhibited by using a polypeptide comprising a binding portion of the respective propeptide, or a variant thereof. Such propeptides may be prepared as fusion proteins, including Fc fusion proteins. Examples of suitable propeptides are disclosed in published patent applications WO 02/085306 and WO 06/002387.

Additionally, other binding proteins, such as the so-called "traps" (e.g., follistatin, FLRG, FSTL, Cerberus and Coco), soluble type I receptors, e.g., ALK-7 may be used. Examples of such polypeptides may be found in published patent applications WO 05/115439, WO 08/109779, WO 08/067480, WO 07/109686, WO 05/100563, and WO 05/025601.

Nucleic acids, such as antisense or RNAi probes (which may include both naturally and non-naturally occurring nucleotides) may be used to inhibit expression of ActRIIB or any of the ligands discussed herein.

5. Screening Assays

In certain aspects, the present invention relates to the use of the subject ActRIIB polypeptides (e.g., soluble ActRIIB polypeptides) to identify compounds (agents) which are agonist or antagonists of the ActRIIB polypeptides. Compounds identified through this screening can be tested in tissues such as fat, muscle, bone, cartilage, and/or neurons, to assess their ability to modulate tissue growth in vitro. Optionally, these compounds can further be tested in animal models to assess their ability to modulate tissue growth in vivo.

There are numerous approaches to screening for therapeutic agents for modulating tissue growth by targeting the ActRIIB polypeptides. In certain embodiments, high-throughput screening of compounds can be carried out to identify agents that perturb ActRIIB-mediated effects on growth of fat, muscle, bone, cartilage, and/or neurons. In certain embodiments, the assay is carried out to screen and identify compounds that specifically inhibit or reduce binding of an ActRIIB polypeptide to its binding partner, such as an ActRIIB ligand (e.g., activin, GDF3, Nodal, GDF8, or GDF11). Alternatively, the assay can be used to identify compounds that enhance binding of an ActRIIB polypeptide to its binding protein such as an ActRIIB ligand. In a further embodiment, the compounds can be identified by their ability to interact with an ActRIIB polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIB polypeptide and its binding protein (e.g., an ActRIIB ligand).

Merely to illustrate, in an exemplary screening assay of the present invention, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added a composition containing an ActRIIB ligand. Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIB polypeptide and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or fluorescently labeled (e.g., FITC), or enzymatically labeled ActRIIB polypeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRIIB polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRIIB polypeptide and its binding protein. See for example, U.S. Pat. No. 5,283,317; Zervos et al., 1993, Cell 72:223-232; Madura et al., 1993, J Biol Chem 268:12046-12054; Bartel et al., 1993, Biotechniques 14:920-924; and Iwabuchi et al., 1993, Oncogene 8:1693-1696). In a specific embodiment, the present invention contemplates the use of reverse two hybrid systems to identify compounds (e.g., small molecules or peptides) that dissociate interactions between an ActRIIB polypeptide and its binding protein. See for example, Vidal and Legrain, 1999, Nucleic Acids Res 27:919-29; Vidal and Legrain, 1999, Trends Biotechnol 17:374-81; and U.S. Pat. Nos. 5,525,490; 5,955,280; and 5,965,368.

In certain embodiments, the subject compounds are identified by their ability to interact with an ActRIIB polypeptide of the invention. The interaction between the compound and the ActRIIB polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an ActRIIB polypeptide. This may include a solid phase or fluid phase binding event. Alternatively, the gene encoding an ActRIIB polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for controlling weight gain and obesity. At the cellular level, adipocyte proliferation and differentiation is critical in the development of obesity, which leads to the generation of additional fat cells (adipocytes). Therefore, any compound identified can be tested in whole cells or tissues, in vitro or in vivo, to confirm their ability to modulate adipogenesis by measuring adipocyte proliferation or differentiation. Various methods known in the art can be utilized for this purpose. For example, the effect of an ActRIIB polypeptide (e.g., a soluble ActRIIB polypeptide) or test compounds on adipogenesis can be determined by measuring differentiation of 3T3-L1 preadipocytes to mature adipocytes in cell based assays, such as, by observing the accumulation of triacylglycerol in Oil Red O staining vesicles and by the appearance of certain adipocyte markers such as FABP (aP2/422) and PPARγ2. See, for example, Reusch et al., 2000, Mol Cell Biol. 20:1008-20; Deng et al., 2000, Endocrinology. 141:2370-6; Bell et al., 2000, Obes Res. 8:249-54. Another example of cell-based assays includes analyzing the role of ActRIIB polypeptides and test compounds in proliferation of adipocytes or adipocyte precursor cells (e.g., 3T3-L1 cells), such as, by monitoring bromodeoxyuridine (BrdU)-positive cells. See, for example, Pico et al., 1998, Mol Cell Biochem. 189:1-7; Masuno et al., 2003, Toxicol Sci. 75:314-20.

It is understood that the screening assays of the present invention apply to not only the subject ActRIIB polypeptides and variants of the ActRIIB polypeptides, but also any test compounds including agonists and antagonist of the ActRIIB polypeptides or ActRIIB signaling. Further, these screening assays are useful for drug target verification and quality control purposes.

6. Exemplary Therapeutic Uses

In certain embodiments, compositions (e.g., ActRIIB polypeptides) of the present invention can be used for treating or preventing a disease or condition that is associated with abnormal activity of an ActRIIB polypeptide and/or an ActRIIB ligand (e.g., activin or GDF8). In certain embodiments, the present invention provides methods of treating or preventing an individual in need thereof through administering to the individual a therapeutically effective amount of an ActRIIB polypeptide as described above. These methods are particularly aimed at therapeutic and prophylactic treatments of animals, and more particularly, humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established.

As demonstrated herein, ActRIIB-Fc promotes the expression of UCP1, a protein that mediates an uncoupling in mitochondria, leading to metabolically active, or thermogenic, adipose tissue. Accordingly, compositions disclosed herein may be used to treat a variety of disorders, such as a deficiency in brown adipose tissue or brown adipocytes, metabolic syndrome (also known as syndrome X), diabetes, hyperlipidemia, hypercholesterolemia, overeating and bulimia, hypertension, arteriosclerosis (coronary artery disease or coronary heart disease), myocardial infarction, congestive heart failure, cerebral infarction, cerebral thrombosis, respiratory disorders (such as Pickwickian syndrome), cancers of the colon, prostate, breast, endometrium, and kidney, growth hormone-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

In certain embodiments, compositions (e.g., soluble ActRIIB polypeptides) of the invention are used to promote formation and/or activity of thermogenic adipocytes. As discussed above, thermogenic discrete brown-adipose tissue and brown adiopocytes within white adipose tissue contain large numbers of mitochondria expressing uncoupling protein-1 (UCP). Individuals with high caloric intake and lacking brown adipocytes are unable to convert excess caloric intake to heat and are therefore compelled to store unused biochemical energy, typically as enlarged white adipose tissue. Blocking or antagonizing function of one or more ActRIIB ligands (e.g., GDF8) in vivo can effectively increase thermogenic activity of brown adipocytes in discrete depots or of brown adiopocytes distributed within white adipose tissue. This approach is confirmed and supported by the data shown herein, whereby an ActRIIB-Fc protein was shown to induce UCP1 expression in white fat, enhance overall body composition, and improve metabolic status in mice on a high-fat diet.

In certain embodiments, compositions (e.g., soluble ActRIIB polypeptides) of the invention are used as part of a treatment for metabolic syndrome (also known as syndrome X and insulin resistance syndrome), which is a combination of disorders and risk factors that increase the risk of developing cardiovascular disease and diabetes mellitus type II. Most patients are older, obese, sedentary, and have some degree of insulin resistance. Central (abdominal or visceral) adiposity is a significant feature of the syndrome.

In related embodiments, soluble ActRIIB polypeptides and other compositions of the invention can be used as part of a treatment for diabetes mellitus type II (also known as non-insulin-dependent diabetes mellitus or adult-onset diabetes), which is characterized by elevated blood glucose in the context of insulin resistance and relative insulin deficiency. Complex and multifactorial metabolic changes in diabetes often lead to damage and functional impairment of many organs, most importantly the cardiovascular system. Diabetes mellitus type II is often associated with obesity (abdominal or visceral adiposity), hypertension, elevated cholesterol, and metabolic syndrome. Important risk factors for diabetes mellitus type II include aging, high-fat diets, and a sedentary lifestyle.

In other related embodiments, soluble ActRIIB polypeptides and other compositions of the invention can be used as part of a treatment for atherosclerosis, a chronic inflammatory condition in which artery walls thicken due to the accumulation of fatty deposits, often referred to as plaques. Risk factors for atherosclerosis include aging, diabetes mellitus, dyslipoproteinemia, obesity (abdominal or visceral adiposity), and a sedentary lifestyle.

Soluble ActRIIB polypeptides can also be used for lipodystrophic disorders, which tend to be associated with metabolic syndrome. Severe insulin resistance can result from both genetic and acquired forms of lipodystrophy, including in the latter case human immunodeficiency virus (HIV)-related lipodystrophy in patients treated with antiretroviral therapy.

The subject ActRIIB polypeptides may further be used as a therapeutic agent for slowing or preventing the development of obesity. This approach is confirmed and supported by the data shown herein, whereby an ActRIIB-Fc protein was shown to improve metabolic status in mice on a high-fat diet.

In other embodiments, the present invention provides compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof an ActRIIB polypeptide.

In one specific embodiment, the present invention relates to methods and compounds for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass.

As demonstrated in WO 2006/012627 and WO 2008/097541, compounds disclosed herein stimulate muscle growth. Accordingly, these compounds may be particularly useful in diseases or conditions with overlapping muscle and metabolic dysfunction.

In certain embodiments, compositions (e.g., soluble ActRIIB polypeptides) of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Moreover, declining muscle mass and diminishing physical activity contribute to an imbalance between caloric intake and energy expenditure, leading to unhealthy storage of excess energy as white adipose tissue. Exemplary muscular dystrophies that can be treated with a regimen including the subject ActRIIB polypeptides include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, recent researches demonstrate that blocking or eliminating function of GDF8 (an ActRIIB ligand) in vivo can effectively treat at least certain symptoms in DMD and BMD patients. Thus, the subject ActRIIB polypeptides may act as GDF8 inhibitors (antagonists), and constitute an alternative means of blocking the functions of GDF8 and/or ActRIIB in vivo in DMD and BMD patients. This approach is confirmed and supported by the data shown herein, whereby an ActRIIB-Fc protein was shown to increase muscle mass in a mouse model of muscular dystrophy.

Similarly, the subject ActRIIB polypeptides provide an effective means to increase muscle mass in other disease conditions that are in need of muscle growth. For example, ALS, also called Lou Gehrig's disease (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset. This approach is confirmed and supported by the data shown herein, whereby an ActRIIB-Fc protein was shown to improve the appearance, muscle mass and lifespan of a mouse model of ALS.

ActRIIB polypeptide-induced increased muscle mass might also benefit those suffering from muscle wasting diseases. Gonzalez-Cadavid et al. (supra) reported that that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Sarcopenia, the loss of muscle with aging is also often associated with metabolic syndrome, diabetes, arteriosclerosis, dyslipidemia, and other age-related metabolic conditions. ActRIIB polypeptide-induced muscle mass might also benefit those suffering from sarcopenia.

7. Pharmaceutical Compositions

In certain embodiments, compounds (e.g., ActRIIB polypeptides) of the present invention are formulated with a pharmaceutically acceptable carrier. For example, an ActRIIB polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neurons), for example, a site having a tissue damage. Topical administration may be suitable for wound healing and tissue repair. Therapeutically useful agents other than the ActRIIB polypeptides which may also optionally be included in the composition as described above, may alternatively or additionally, be administered simultaneously or sequentially with the subject compounds (e.g., ActRIIB polypeptides) in the methods of the invention.

In certain embodiments, compositions of the present invention may include a matrix capable of delivering one or more therapeutic compounds (e.g., ActRIIB polypeptides) to a target tissue site, providing a structure for the developing tissue and optimally capable of being resorbed into the body. For example, the matrix may provide slow release of the ActRIIB polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., an ActRIIB polypeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more ActRIIB polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRIIB polypeptides). The various factors will depend upon the disease to be treated.

In certain embodiments, the present invention also provides gene therapy for the in vivo production of ActRIIB polypeptides or other compounds disclosed herein. Such therapy would achieve its therapeutic effect by introduction of the ActRIIB polynucleotide sequences into cells or tissues having the disorders as listed above. Delivery of ActRIIB polynucleotide sequences can be achieved using a recombinant expression vector such as a chimeric virus or a colloidal dispersion system. Preferred for therapeutic delivery of ActRIIB polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIB polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIB polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Generation of an ActRIIB-Fc Fusion Protein

Applicants constructed a soluble ActRIIB fusion protein that has the extracellular domain of human ActRIIB fused to a human or mouse Fc domain with a minimal linker (three glycine amino acids) in between. The constructs are referred to as ActRIIB(20-134)-hFc and ActRIIB(20-134)-mFc, respectively.

ActRIIB-hFc is shown below as purified from CHO cell lines (SEQ ID NO: 5)

GRGEAETRECIYYNANWELERTNQSGLERCEGEQDKRLHCYASWRNSSGTI

ELVKKGCWLDDFNCYDRQECVATEENPQVYFCCCEGNFCNERFTHLPEAGG

PEVTYEPPPTAPT<u>GGGTHTCPPCPAPELLGGPSVFLFPPKPKDTLMISRTP</u>

<u>EVTCVVVDVSHEDPEVKFNWYVDGVEVHNAKTKPREEQYNSTYRVVSVLTV</u>

<u>LHQDWLNGKEYKCKVSNKALPVPIEKTISKAKGQPREPQVYTLPPSREEMT</u>

<u>KNQVSLTCLVKGFYPSDIAVEWESNGQPENNYKTTPPVLDSDGSFFLYSKL</u>

<u>TVDKSRWQQGNVFSCSVMHEALHNHYTQKSLSLSPGK</u>

The ActRIIB(20-134)-hFc and ActRIIB(20-134)-mFc proteins were expressed in CHO cell lines. Three different leader sequences were considered:

```
(i) Honey bee mellitin (HBML):
                                              (SEQ ID NO: 7)
    MKFLVNVALVFMVVYISYIYA (ii) Tissue Plasminogen Activator (TPA):
                                              (SEQ ID NO: 8)
    MDAMKRGLCCVLLLCGAVFVSP (iii) Native:
                                              (SEQ ID NO: 9)
    MGAAAKLAFAVFLISCSSGA.
```

The selected form employs the TPA leader and has the following unprocessed amino acid sequence:

(SEQ ID NO: 17)
<u>MDAMKRGLCCVLLLCGAVFVSP</u>GASGRGEAETRECIYYNANWELERTNQS

GLERCEGEQDKRLHCYASWRNSSGTIELVKKGCWLDDFNCYDRQECVATE

ENPQVYFCCCEGNFCNERFTHLPEAGGPEVTYEPPPTAPT<u>GGGTHTCPPC</u>

<u>PAPELLGGPSVFLFPPKPKDTLMISRTPEVTCVVVDVSHEDPEVKFNWYV</u>

<u>DGVEVHNAKTKPREEQYNSTYRVVSVLTVLHQDWLNGKEYKCKVSNKALP</u>

<u>VPIEKTISKAKGQPREPQVYTLPPSREEMTKNQVSLTCLVKGFYPSDIAV</u>

<u>EWESNGQPENNYKTTPPVLDSDGSFFLYSKLTVDKSRWQQGNVFSCSVMH</u>

<u>EALHNHYTQKSLSLSPGK</u>

This polypeptide is encoded by the following nucleic acid sequence (SEQ ID NO:10):

```
A TGGATGCAAT GAAGAGAGGG CTCTGCTGTG TGCTGCTGCT

GTGTGGAGCA GTCTTCGTTT CGCCCGGCGC CTCTGGGCGT

GGGGAGGCTG AGACACGGGA GTGCATCTAC TACAACGCCA

ACTGGGAGCT GGAGCGCACC AACCAGAGCG GCCTGGAGCG

CTGCGAAGGC GAGCAGGACA AGCGGCTGCA CTGCTACGCC

TCCTGGCGCA ACAGCTCTGG CACCATCGAG CTCGTGAAGA

AGGGCTGCTG GCTAGATGAC TTCAACTGCT ACGATAGGCA

GGAGTGTGTG GCCACTGAGG AGAACCCCCA GGTGTACTTC
```

```
TGCTGCTGTG AAGGCAACTT CTGCAACGAG CGCTTCACTC

ATTTGCCAGA GGCTGGGGGC CCGGAAGTCA CGTACGAGCC

ACCCCCGACA GCCCCCACCG GTGGTGGAAC TCACACATGC

CCACCGTGCC CAGCACCTGA ACTCCTGGGG GGACCGTCAG

TCTTCCTCTT CCCCCCAAAA CCCAAGGACA CCCTCATGAT

CTCCCGGACC CCTGAGGTCA CATGCGTGGT GGTGGACGTG

AGCCACGAAG ACCCTGAGGT CAAGTTCAAC TGGTACGTGG

ACGGCGTGGA GGTGCATAAT GCCAAGACAA AGCCGCGGGA

GGAGCAGTAC AACAGCACGT ACCGTGTGGT CAGCGTCCTC

ACCGTCCTGC ACCAGGACTG GCTGAATGGC AAGGAGTACA

AGTGCAAGGT CTCCAACAAA GCCCTCCCAG TCCCCATCGA

GAAAACCATC TCCAAAGCCA AAGGGCAGCC CCGAGAACCA

CAGGTGTACA CCCTGCCCCC ATCCCGGGAG GAGATGACCA

AGAACCAGGT CAGCCTGACC TGCCTGGTCA AAGGCTTCTA

TCCCAGCGAC ATCGCCGTGG AGTGGGAGAG CAATGGGCAG

CCGGAGAACA ACTACAAGAC CACGCCTCCC GTGCTGGACT

CCGACGGCTC CTTCTTCCTC TATAGCAAGC TCACCGTGGA

CAAGAGCAGG TGGCAGCAGG GGAACGTCTT CTCATGCTCC

GTGATGCATG AGGCTCTGCA CAACCACTAC ACGCAGAAGA

GCCTCTCCCT GTCTCCGGGT AAATGA
```

N-terminal sequencing of the CHO-cell produced material revealed a major sequence of -GRGEAE (SEQ ID NO: 11). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

ActRIIB-Fc fusion proteins were also expressed in HEK293 cells and COS cells. Although material from all cell lines and reasonable culture conditions provided protein with muscle-building activity in vivo, variability in potency was observed perhaps relating to cell line selection and/or culture conditions.

Example 2

Generation of ActRIIB-Fc Mutants

Applicants generated a series of mutations in the extracellular domain of ActRIIB and produced these mutant proteins as soluble fusion proteins between extracellular ActRIIB and an Fc domain. The background ActRIIB-Fc fusion has the sequence (Fc portion underlined)(SEQ ID NO:12):

```
SGRGEAETRECIYYNANWELERTNQSGLERCEGEQDKRLHCYASWR

NSSGTIELVKKGCWLDDFNCYDRQECVATEENPQVYFCCCEGNFCN

ERFTHLPEAGGPEVTYEPPPTAPTGGGTHTCPPCPAPELLGGPSVF

LFPPKPKDTLMISRTPEVTCVVVDVSHEDPEVKFNWYVDGVEVHNA

KTKPREEQYNSTYRVVSVLTVLHQDWLNGKEYKCKVSNKALPVPIE

KTISKAKGQPREPQVYTLPPSREEMTKNQVSLTCLVKGFYPSDIAV

EWESNGQPENNYKTTPPVLDSDGSFFLYSKLTVDKSRWQQGNVFSC

SVMHEALHNHYTQKSLSLSPGK
```

Various mutations, including N- and C-terminal truncations, were introduced into the background ActRIIB-Fc protein. Based on the data presented in Example 1, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into E. coli DH5 alpha, colonies were picked and DNAs were isolated. For murine constructs (mFc), a murine IgG2a was substituted for the human IgG1. All mutants were sequence verified.

All of the mutants were produced in HEK293T cells by transient transfection. In summary, in a 500 ml spinner, HEK293T cells were set up at $6 \times 10^5$ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, protein A column and eluted with low pH (3.0) glycine buffer. After neutralization, these were dialyzed against PBS.

Mutants were also produced in CHO cells by similar methodology.

Mutants were tested in binding assays and/or bioassays. In some instances, assays were performed with conditioned medium rather than purified proteins. Variants are described, for example, in published patent applications WO 06/012627 and WO 08/097541. Such variants may be used in the methods described herein.

Example 3

Effect of ActRIIB(20-134)-hFc on Thermogenic Properties of White Adipose Tissue in Mice Fed a High-Fat Diet Applicants investigated the effects of ActRIIB-Fc on brown adipocytes and other metabolic endpoints in male mice fed a high-fat diet. Ten-week-old C57BL/6 mice were weight-matched and treated with ActRIIB(20-134)-hFc (n=10) or Tris-buffered-saline (TBS) vehicle (n=7) twice per week at 10 mg/kg, s.c., for 60 days. During this period, mice had unlimited access to a diet containing 58% fat instead of the standard chow containing 4.5% fat. At study termination, epididymal fat pads were collected, and quantitative RT-PCR (reverse transcription polymerase chain reaction) was used to measure levels of mRNA encoding uncoupling protein-1 (UCP1), a well-documented marker of thermogenic capability in brown adipocytes, which are diffusely distributed within white adipose depots (Cousin et al., 1992, J Cell Sci 103:931-942).

ActRIIB(20-134)-hFc treatment caused a constellation of noteworthy metabolic effects. In mice on the high-fat diet, ActRIIB(20-134)-hFc increased UCP1 mRNA levels in epididymal fat nearly nine-fold compared to vehicle (FIG. 1; P<0.05), a particularly impressive effect given that C57BL/6 mice display severely blunted induction of UCP1 and brown adipocytes within key white fat depots compared to other mouse strains (Guerra et al., 1998, J Clin Invest 102:412-420; Xue et al., 2007, J Lipid Res 48:41-51). ActRIIB(20-134)-hFc also produced a beneficial, 30% reduction (P<0.001) of serum free fatty acid concentrations. Importantly, upregulation of UCP1 was accompanied by beneficial effects of ActRIIB(20-134)-hFc on body composition, as determined by nuclear magnetic resonance (NMR) at baseline and Day 48. Under high-fat dietary conditions, total fat mass in vehicle-treated controls tripled during this 48-day period, and ActRIIB(20-134)-hFc treatment cut this increase by 40%. By Day 48, total fat mass was 26% of body weight in ActRIIB(20-134)-hFc-treated mice vs. 39% in control mice, whereas lean tissue mass was 64% of body weight in ActRIIB-Fc-treated mice vs. 55% in control mice. Thus, the net result was a healthier body composition under conditions of high-fat diet.

Example 4

Effect of Truncated Variant ActRIIB(25-131)-hFc on Thermogenic Properties of White Adipose Tissue in Mice Fed a High-Fat Diet In the study described above (Example 3), Applicants also investigated effects of the truncated variant ActRIIB(25-131)-hFc on thermogenic properties of white adipose tissue and other metabolic endpoints under high-fat dietary conditions.

Applicants generated a truncated fusion protein ActRIIB(25-131)-hFc (FIGS. 13-14), using the same leader and methodology as described above with respect to ActRIIB(20-134)-hFc. The mature protein purified after expression in CHO cells has the sequence shown below (SEQ ID NO: 6):

```
ETRECIYYNA NWELERTNQS GLERCEGEQD KRLHCYASWR

NSSGTIELVK KGCWLDDFNC YDRQECVATE ENPQVYFCCC

EGNFCNERFT HLPEAGGPEV TYEPPPTGGG THTCPPCPAP

ELLGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSREEMTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

Ten-week-old C57BL/6 mice were treated with ActRIIB(25-131)-hFc, at 10 mg/kg, s.c., or Tris-buffered-saline (TBS) vehicle twice per week for 60 days. During this period, mice had unlimited access to a diet containing 58% fat instead of the standard chow containing 4.5% fat. An additional group of mice maintained on the standard chow diet were also treated with TBS vehicle and followed as a dietary control.

Figure 2:
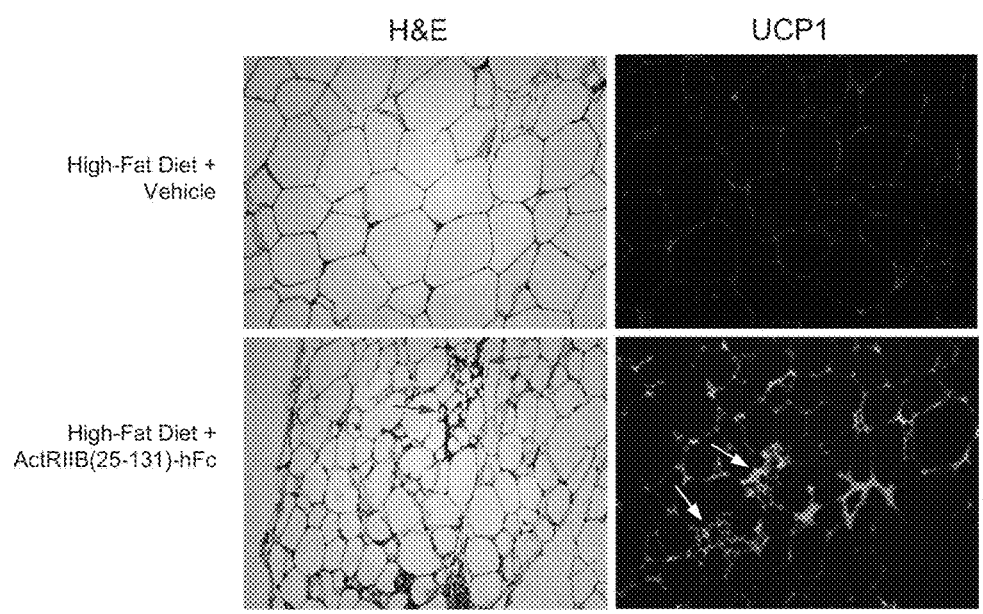
FIG. 2 shows thermogenic histological changes induced within epididymal white adipose tissue by ActRIIB(25-131)-hFc treatment for 60 days in mice fed a high-fat diet. All microscopic images shown at the same magnification. Hematoxylin and eosin (H&E) staining indicates the ability of ActRIIB(25-131)-hFc to reduce lipid droplet size and induce clusters of multilocular adipocytes (arrows) characteristic of brown fat. Immunostaining of non-adjacent sections reveals widespread cytoplasmic induction of UCP1 (green fluorescence) in both multilocular and unilocular adipocytes.

Under high-fat dietary conditions, ActRIIB(25-131)-hFc treatment triggered histological changes and a gene expression profile in white adipose tissue that were consistent with thermogenic capability. As shown in FIG. 2, histological examination of epididymal white fat indicated that ActRIIB(25-131)-hFc reduced lipid droplet size and caused formation of clusters of multilocular adipocytes that are a hallmark of brown fat. Moreover, immunohistochemical analysis of this tissue revealed widespread cytoplasmic induction of UCP1 in both multilocular and unilocular adipocytes as a result of ActRIIB(25-131)-hFc treatment (FIG. 2).

Figure 3:
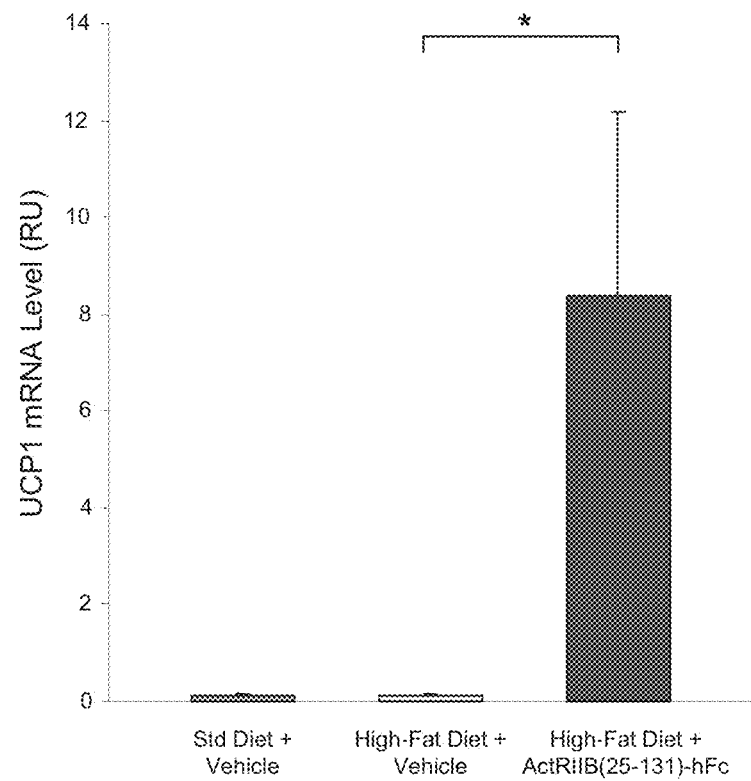
FIG. 3 shows the effect of ActRIIB(25-131)-hFc treatment for 60 days on UCP1 mRNA levels in epididymal white fat of mice fed a high-fat diet. RT-PCR data (in relative units, RU) are means±SEM; n=6-7 per group; *, $p<0.05$. ActRIIB(25-131)-hFc caused a 60-fold increase in mRNA encoding this selective marker for brown fat, thus indicating upregulation of thermogenic capability within this white fat depot.
Figure 4:
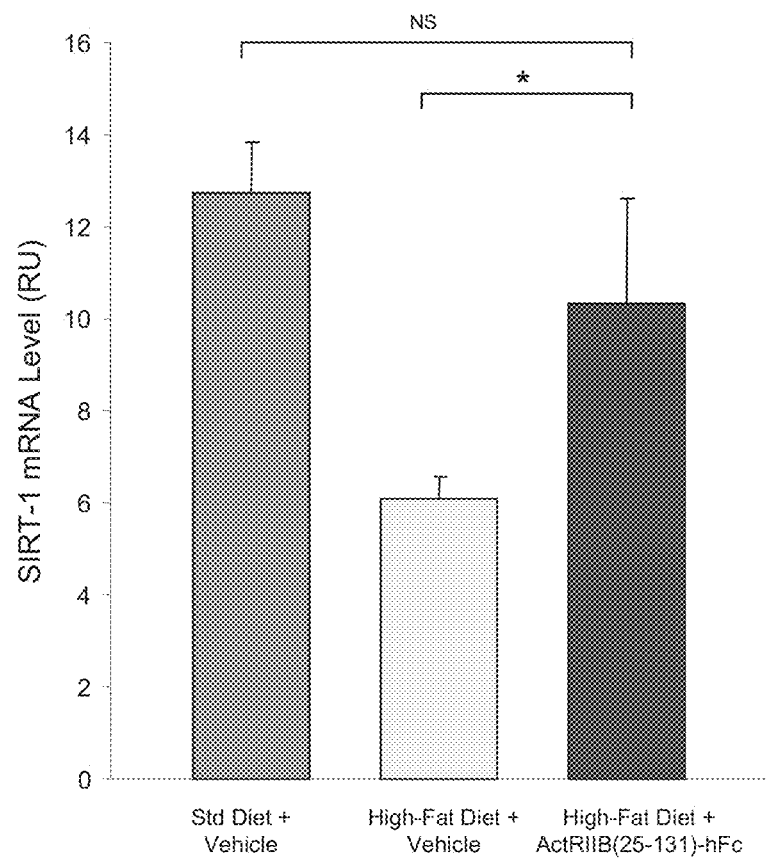
FIG. 4 shows levels of mRNA encoding the sirtuin family member SIRT-1 (silent information regulator two, homolog 1) in epididymal white fat of mice as a function of diet and ActRIIB(25-131)-hFc treatment for 60 days. RT-PCR data (in relative units, RU) are means±SEM; n=7 per group; *, $p<0.05$; NS=not significant. In mice fed a high-fat diet, ActRIIB(25-131)-hFc increased SIRT-1 mRNA levels by more than 70%, restoring them to levels not significantly different from those in mice fed a standard diet.
Figure 5:
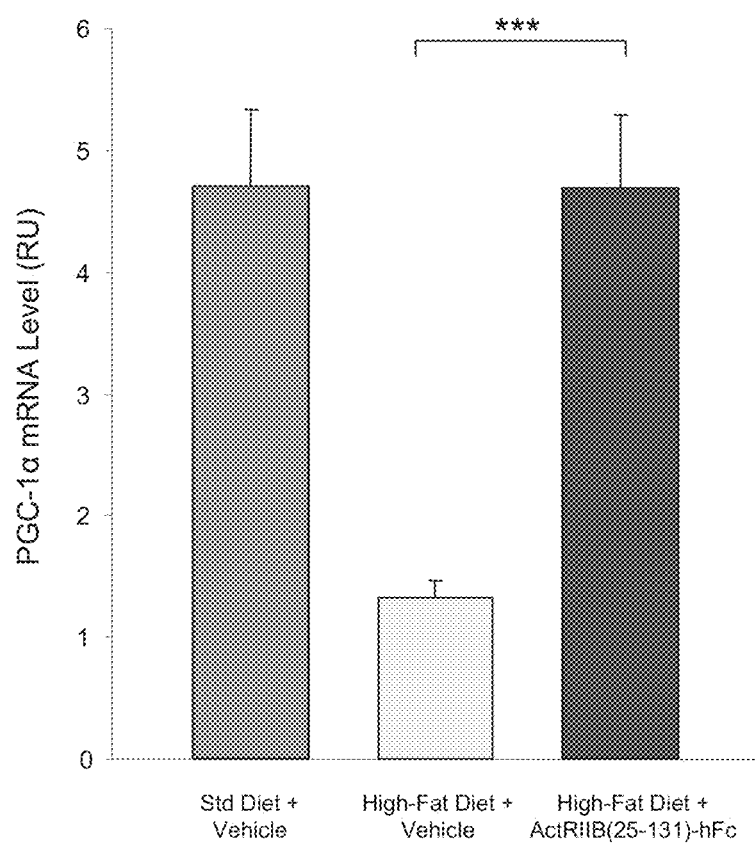
FIG. 5 shows levels of mRNA encoding PGC-1α (peroxisome proliferator-activated receptor gamma coactivator-1α) in epididymal white fat of mice as a function of diet and ActRIIB(25-131)-hFc treatment for 60 days. RT-PCR data (in relative units, RU) are means±SEM; n=6-7 per group; ***, $p<0.001$. In mice fed a high-fat diet, ActRIIB(25-131)-hFc increased PGC-1α mRNA levels by more than 250%, restoring them to levels not significantly different from those in mice fed a standard diet.

Accompanying these histological changes were significant changes in the expression of key thermogenic and metabolic regulatory genes in epididymal white fat, as determined by quantitative RT-PCR. In mice on the high-fat diet, ActRIIB(25-131)-hFc treatment increased UCP 1 mRNA levels more than 60-fold compared to vehicle (FIG. 3), a particularly impressive change since, as noted above, this strain of mouse displays severely blunted induction of UCP1 and brown adipocytes within key white fat depots compared to other mouse strains. In addition, ActRIIB(25-131)-hFc treatment increased levels of mRNA encoding the sirtuin SIRT-1 (silent information regulator two, homolog 1) (FIG. 4), an energy-sensitive master regulator (deacetylase) that protects against metabolic damage induced by a high-fat diet (Pfluger et al., 2008, Proc Natl Acad Sci USA 105: 9793-9798) and is implicated as an important control of fatty acid mobilization (Rodgers et al., 2008, FEBS Lett 582:46-53). Significantly, ActRIIB(25-131)-hFc treatment also increased levels of mRNA encoding PGC-1α (peroxisome proliferator-activated receptor gamma coactivator-1α) (FIG. 5), a well-documented target of SIRT-1 that, in turn, controls expression of many genes necessary for mitochondrial biogenesis and thermogenic capability in brown adiopose tissue (Uldry et al., 2006, Cell Metab, 3:333-341). Notably, forced expression of PGC-1α in white adipocytes has been shown to induce a thermogenic program of gene expression, including UCP1, closely resembling that in brown adipocytes (Hansen et al., 2006, Biochem J 398:153-168). In the present study, ActRIIB(25-131)-hFc restored PGC-1α gene expression in white adipose tissue under high-fat dietary conditions to levels indistinguishable from those in mice fed the standard diet (FIG. 5).

Figure 6:
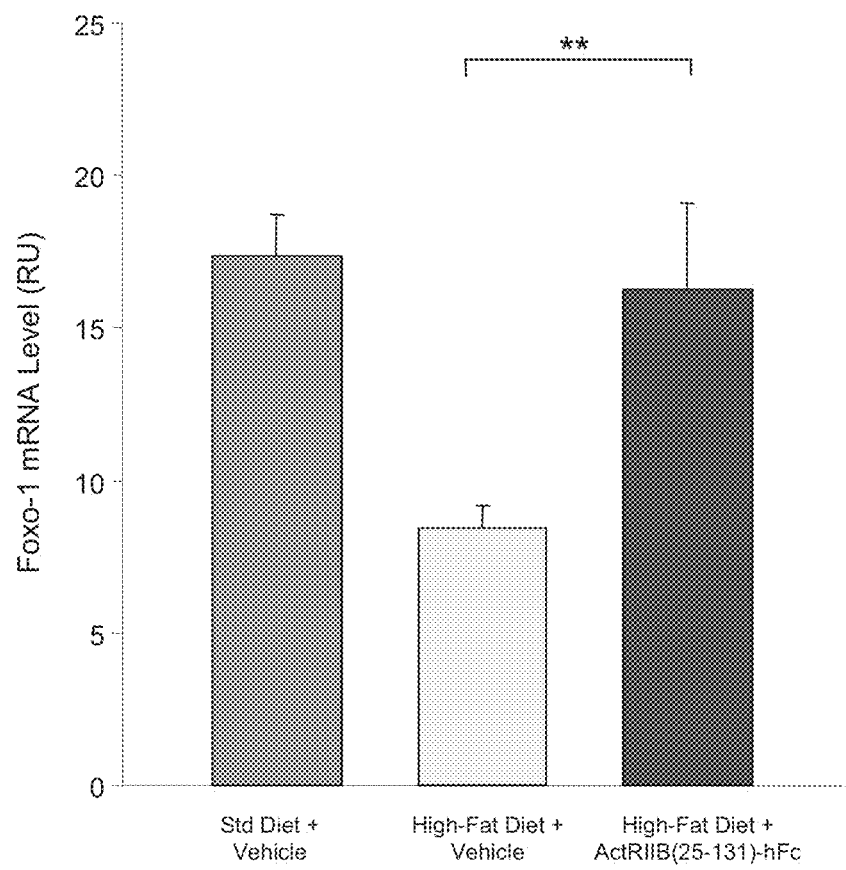
FIG. 6 shows levels of mRNA encoding Foxo-1 (forkhead box-containing, protein O subfamily-1) in epididymal white fat of mice as a function of diet and ActRIIB(25-131)-hFc treatment for 60 days. RT-PCR data (in relative units, RU) are means±SEM; n=7 per group; **, $p<0.01$. In mice fed a high-fat diet, ActRIIB(25-131)-hFc increased Foxo-1 mRNA levels by more than 90%, restoring them to levels not significantly different from those in mice fed a standard diet.
Figure 7:
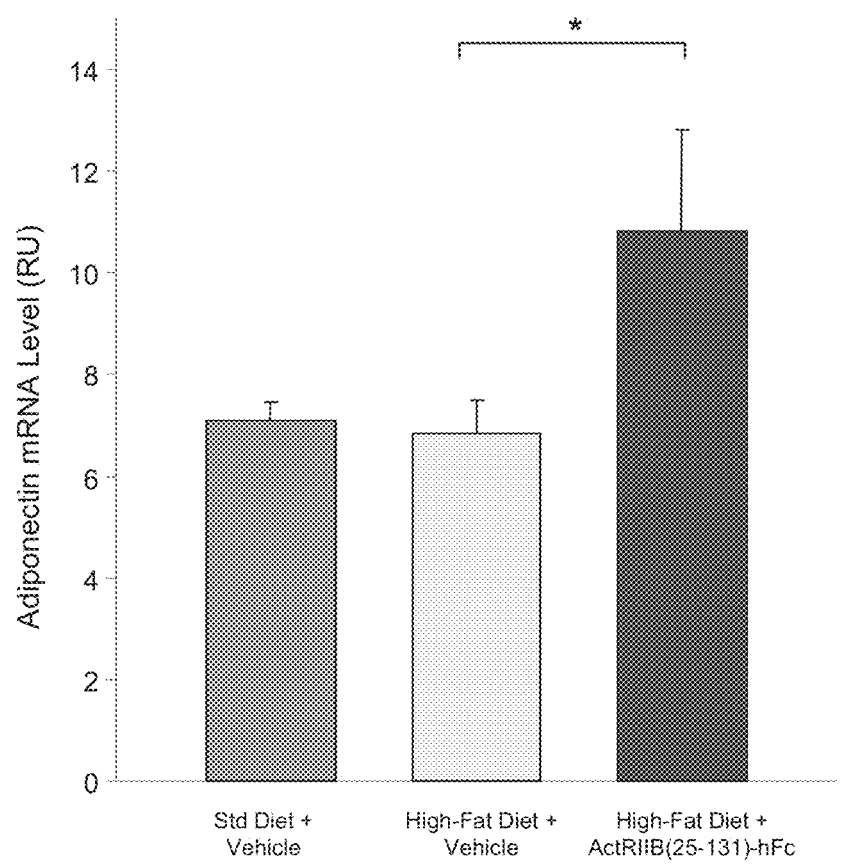
FIG. 7 shows levels of adiponectin mRNA in epididymal white fat of mice as a function of diet and ActRIIB(25-131)-hFc treatment for 60 days. RT-PCR data (in relative units, RU) are means±SEM; n=7 per group; *, $p<0.05$. In mice fed a high-fat diet, ActRIIB(25-131)-hFc increased adiponectin mRNA levels by more than 60%, thus contributing to elevated concentrations of circulating adiponectin in these mice.
Figure 8:
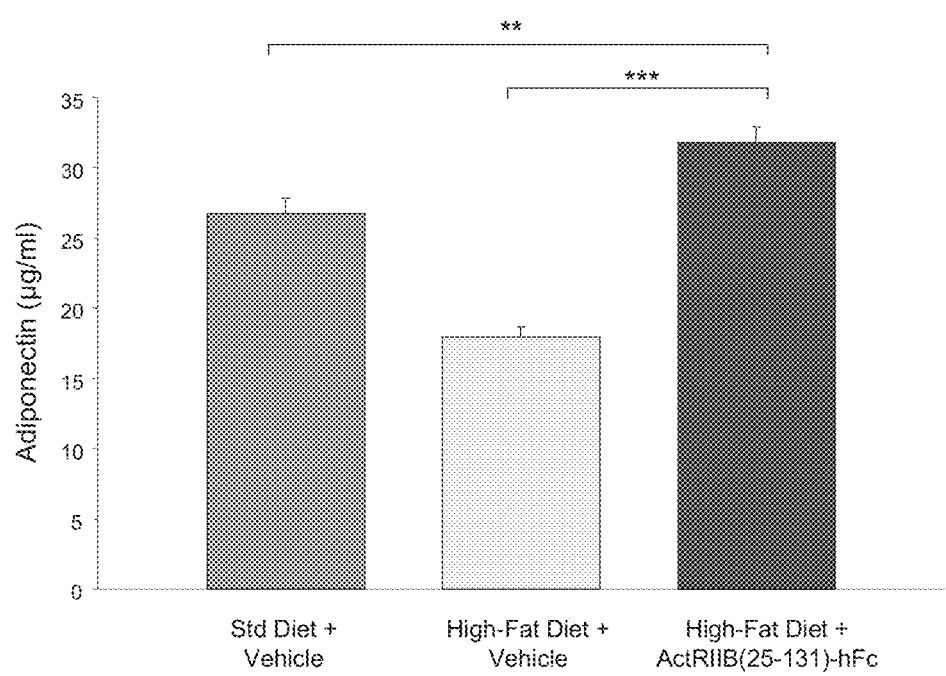
FIG. 8 shows serum levels of adiponectin in mice as a function of diet and ActRIIB(25-131)-hFc treatment for 60 days. ELISA measurements detect all main oligomeric isoforms (total adiponectin), and data are means±SEM; n=7-8 per group; , $p<0.01$; *, $p<0.001$. In mice fed a high-fat diet, ActRIIB(25-131)-hFc increased circulating adiponectin concentrations by more than 75% to significantly exceed those in standard-diet controls.
Figure 9:
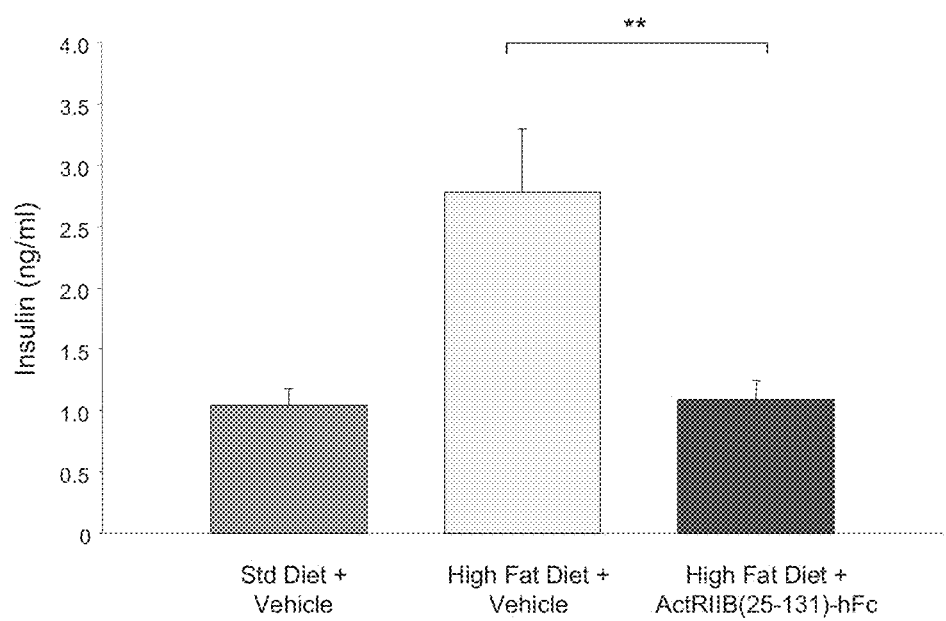
FIG. 9 shows serum concentrations of insulin in mice as a function of diet and ActRIIB(25-131)-hFc treatment for 60 days. Data are means±SEM; n=7-8 per group; **, $p<0.01$. In mice fed a high-fat diet, ActRIIB(25-131)-hFc normalized insulin concentrations to levels observed in standard-diet controls.

Additional changes associated with treatment constitute a prominent link between the altered expression profile in white adipose tissue and beneficial hormonal and metabolic effects. Thus, in epididymal white fat, ActRIIB(25-131)-hFc increased levels of mRNA encoding Foxo-1 (forkhead box-containing, protein 0 subfamily-1) (FIG. 6), a transcription factor that is both a target of SIRT-1 and a key inducer of adiponectin expression (Qiao et al., 2006, J Biol Chem 281:39915-39924). Adiponectin, a fat-derived hormone whose concentration varies inversely with fat mass/obesity, exerts important insulin-sensitizing actions in target tissues (Yamauchi et al., 2001, Nat Med 7:941-946; Maeda et al., 2002, Nat Med 8:731-737; Kadowaki et al., 2005, Endocr Rev 26:439-451). Consistent with Foxo-1 mRNA induction, ActRIIB(25-131)-hFc treatment raised levels of adiponectin mRNA in epididymal white fat (FIG. 7) as well as circulating concentrations of adiponectin (FIG. 8). Importantly, these changes were accompanied in ActRIIB(25-131)-hFc-treated mice by robust decreases in circulating insulin (FIG. 9), triglycerides, free fatty acids, high-density lipoprotein (HDL), and low-density lipoprotein (LDL), leading to normalization of nearly all of these parameters. Finally, the aforementioned effects were accompanied by beneficial changes in body composition, as determined by nuclear magnetic resonance (NMR) at baseline and Day 48. Specifically, total fat mass in vehicle-treated controls under high-fat dietary conditions tripled during this 48-day period, and ActRIIB(25-131)-hFc treatment cut this increase by nearly 40%. In summary, ActRIIB(25-131)-hFc treatment under high-fat dietary conditions resulted in 1) histological changes and a gene expression profile in white adipose tissue that were consistent with thermogenic capability, 2) beneficial changes in a wide range of hormonal and metabolic parameters, and 3) improved body composition.

Example 5

Effect of ActRIIB(25-131)-mFc on Brown Fat Depots in Mice Fed a High-Fat Diet

In another study, Applicants investigated effects of the truncated variant ActRIIB(25-131)-mFc on properties of intrascapular brown fat depots under high-fat dietary conditions. Nine-week-old C57BL/6 mice were treated with ActRIIB(25-131)-mFc (n=20), at 10 mg/kg, s.c., or Tris-buffered-saline (TBS) vehicle (n=10) twice per week for 60 days. Beginning 7 days before the start of dosing, mice had unlimited access to a diet containing 58% fat instead of the standard chow containing 4.5% fat. An additional group of mice (n=10) maintained on the standard chow diet were also treated with TBS vehicle and followed as a dietary control.

Figure 10:
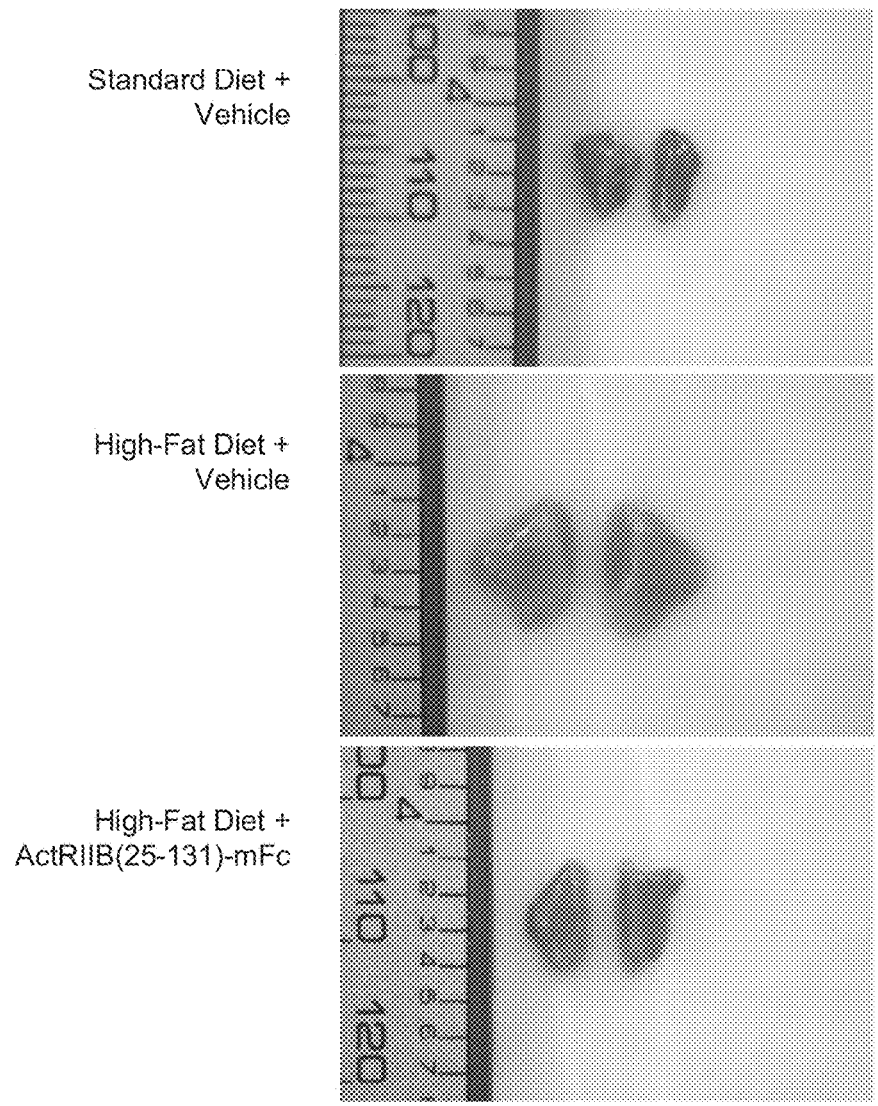
FIG. 10 shows photographs of bilateral pairs of interscapular brown fat depots as a function of diet and ActRIIB (25-131)-mFc treatment for 60 days. High-fat diet increased the size and lightened the color of the depots, whereas ActRIIB(25-131)-mFc largely reversed these changes.
Figure 11:
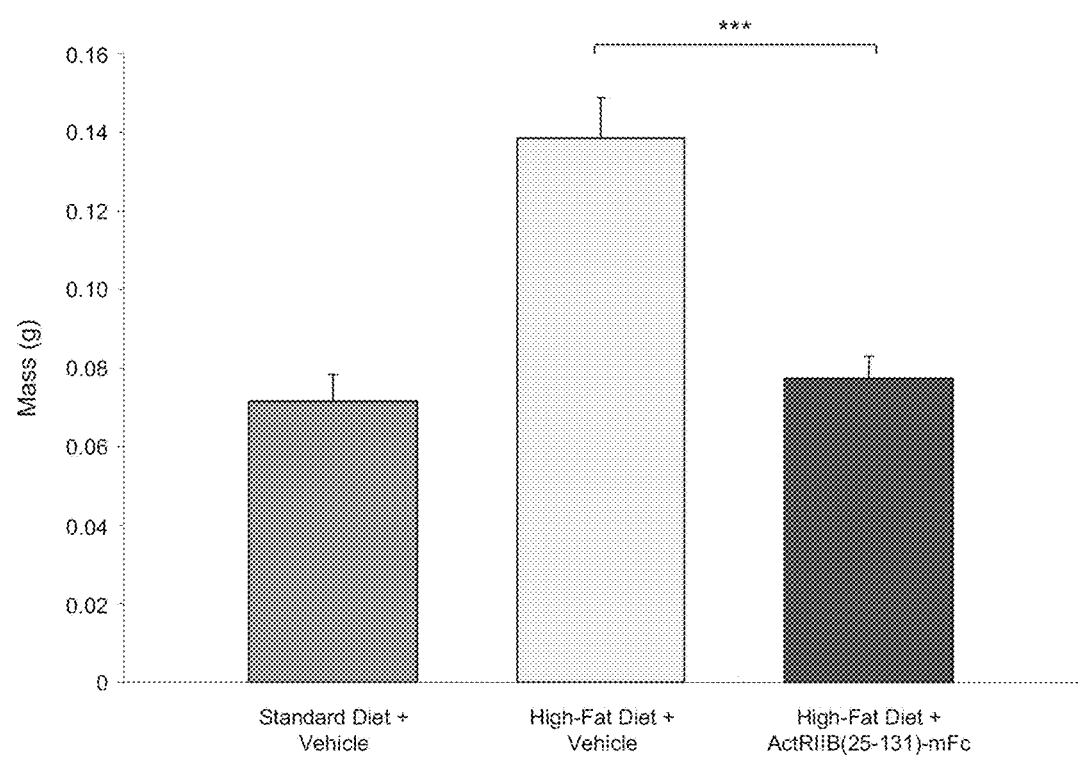
FIG. 11 depicts the effect of ActRIIB(25-131)-mFc treatment for 60 days on the mass of interscapular brown fat in mice fed a high-fat diet. Data are means±SEM for combined left and right depots; ***, $p<0.001$. ActRIIB(25-131)-mFc reversed the effect of high-fat diet on the mass of this brown fat depot.
Figure 12:
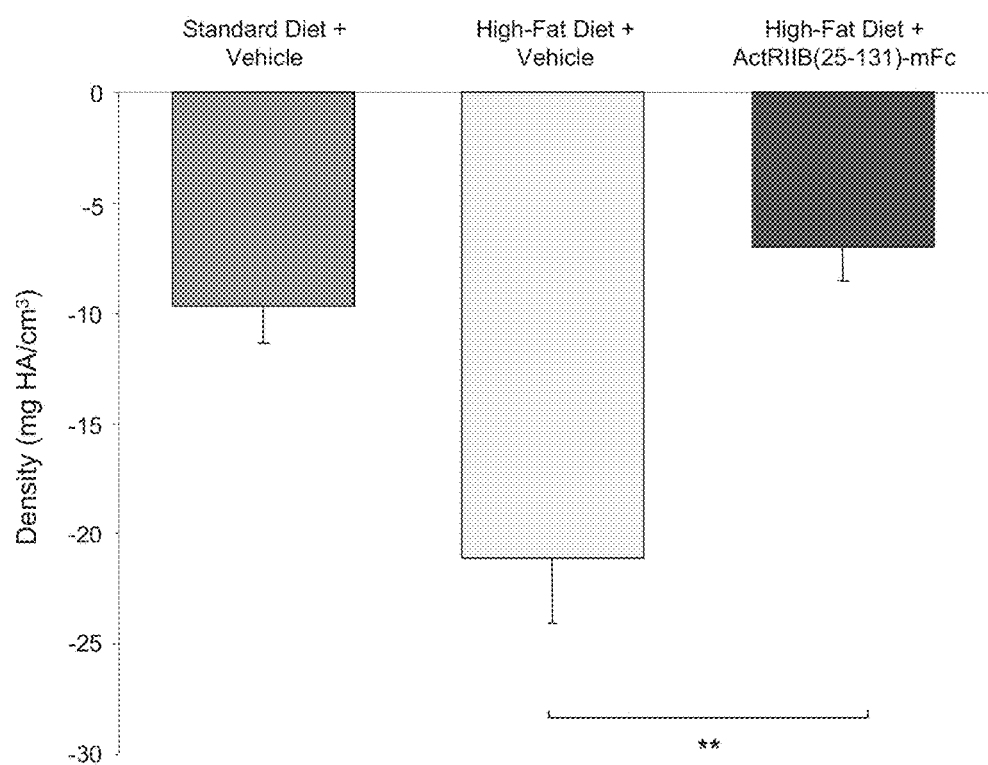
FIG. 12 depicts the effect of ActRIIB(25-131)-mFc treatment for 60 days on the density of interscapular brown fat in mice fed a high-fat diet, as determined by micro-computed tomography (microCT). Data (means±SEM) are expressed in standardized units based on a positive value for the bone mineral hydroxyapatite (HA) and a value of zero for water; therefore, fat values are negative, with values for white fat typically close to −120. **, p<0.01. ActRIIB(25-131)-mFc completely reversed the effect of high-fat diet on the density of this brown fat depot.

Compared to the standard diet, the high-fat diet produced several noticeable changes in the interscapular depot of brown adipose tissue, and ActRIIB(25-131)-mFc treatment either completely or largely reversed each of these changes. Specifically, high-fat diet caused a pronounced enlargement of the interscapular depot as well as lightening of its color from red to pink (FIG. 10). This diet-induced enlargement reflected a doubling of the mass (FIG. 11) and a reduction in the density (FIG. 12) of brown fat depots. Depot density was determined by micro-computed tomography (microCT) in situ for a subset of mice (n=4 per group) whose percentages of total body fat, as determined by nuclear magnetic resonance (NMR), were closest to the group means (all mice were scanned by NMR. In any case, ActRIIB(25-131)-mFc treatment completely reversed diet-induced changes in brown fat mass (FIG. 11) and density (FIG. 12), while largely reversing diet-induced changes in size and color of the depot (FIG. 10). These results indicate that, under high-fat dietary conditions, ActRIIB(25-131)-mFc largely or completely restores properties likely to correlate with healthy brown fat function and thus improves the quality of brown fat as it decreases the overall size of brown fat depots.

Taken together, these data indicate that soluble ActRIIB-Fc fusion proteins can be used as antagonists of signaling by TGF-family ligands to increase the formation and/or activity of thermogenic brown adipocytes, and thereby, to treat metabolic conditions exacerbated by high caloric intake and potentially other conditions as well.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for increasing thermogenic adipocytes in a patient in need thereof, wherein the patient is an adult having an age-related metabolic condition;
   wherein the age-related metabolic condition is selected from the group consisting of: sarcopenia, metabolic syndrome, diabetes, arteriosclerosis, and dyslipidemia; and wherein the patient has a deficiency in brown adipose tissue or brown adipocytes as compared to the levels of brown adipose tissue or brown adipocytes present in one or more healthy control patients;
   the method comprising administering an effective amount of an antibody, or antigen-binding fragment thereof, selected from the group consisting of: an antibody, or antigen-binding fragment thereof, that specifically binds to and inhibits Growth and Differentiation Factor-3 (GDF3); an antibody, or antigen-binding fragment thereof, that specifically binds to and inhibits myostatin; an antibody, or antigen-binding fragment thereof, that specifically binds to and inhibits Growth and Differentiation Factor-11 (GDF11); an antibody, or antigen-binding fragment thereof, that specifically binds to and inhibits nodal; and an antibody, or antigen-binding fragment thereof, that specifically binds to and inhibits activin.

2. The method of claim 1, wherein the antibody, or antigen-binding fragment thereof, is monoclonal.

3. The method of claim 1, wherein the antibody, or antigen-binding fragment thereof, is chimeric.

4. The method of claim 1, wherein the antibody, or antigen-binding fragment thereof, is humanized.

5. The method of claim 1, wherein the antibody, or antigen binding fragment thereof, is selected from: a single chain antibody, a bispecific antibody, a F(ab)2 fragment, and a Fab' fragment.

6. The method of claim 1, wherein the patient has sarcopenia.

7. The method of claim 1, wherein the patient has a metabolic syndrome.

8. The method of claim 1, wherein administration of the antibody, or antigen-binding fragment thereof, promotes uncoupling protein-I (UCP-1) expression in adipocytes of the treated patient.

9. The method of claim 8, wherein the UCP-1 expression is increased in white adipose tissue.

10. The method of claim 1, wherein the antibody, or antigen-binding fragment thereof, specifically binds to and inhibits Growth and Differentiation Factor-3(GDF3).

11. The method of claim 1, wherein the antibody, or antigen-binding fragment thereof, specifically binds to and inhibits Growth and Differentiation Factor-11 (GDF11).

12. The method of claim 1, wherein the antibody, or antigen-binding fragment thereof, specifically binds to and inhibits nodal.

13. The method of claim 1, wherein the antibody, or antigen-binding fragment thereof, specifically binds to and inhibits activin.

14. The method of claim 1, wherein the antibody, or antigen-binding fragment thereof, specifically binds to and inhibits myostatin.

15. The method of claim 1, wherein the patient has diabetes.

16. The method of claim 15, wherein the patient has adult-onset diabetes.

17. The method of claim 1, wherein the patient has arteriosclerosis.

18. The method of claim 1, wherein the patient has dyslipidemia.

* * * * *

SEQUENCE LISTING

```
<160> NUMBER OF SEQ ID NOS: 21

<210> SEQ ID NO 1
<211> LENGTH: 116
<212> TYPE: PRT
<213> ORGANISM: Homo sapiens

<400> SEQUENCE: 1

Ser Gly Arg Gly Glu Ala Glu Thr Arg Glu Cys Ile Tyr Tyr Asn Ala
 1               5                  10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115
```

<210> SEQ ID NO 2
<211> LENGTH: 512
<212> TYPE: PRT
<213> ORGANISM: Homo sapiens

<400> SEQUENCE: 2

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile

```
           370                375                380
Asp Met Tyr Ala Met Gly Leu Val Leu Trp Glu Leu Val Ser Arg Cys
385                 390                395                400

Lys Ala Ala Asp Gly Pro Val Asp Glu Tyr Met Leu Pro Phe Glu Glu
                405                410                415

Glu Ile Gly Gln His Pro Ser Leu Glu Leu Gln Glu Val Val
            420                425                430

His Lys Lys Met Arg Pro Thr Ile Lys Asp His Trp Leu Lys His Pro
            435                440                445

Gly Leu Ala Gln Leu Cys Val Thr Ile Glu Glu Cys Trp Asp His Asp
450                455                460

Ala Glu Ala Arg Leu Ser Ala Gly Cys Val Glu Glu Arg Val Ser Leu
465                 470                475                480

Ile Arg Arg Ser Val Asn Gly Thr Thr Ser Asp Cys Leu Val Ser Leu
                485                490                495

Val Thr Ser Val Thr Asn Val Asp Leu Pro Pro Lys Glu Ser Ser Ile
            500                505                510
```

<210> SEQ ID NO 3
<211> LENGTH: 348
<212> TYPE: DNA
<213> ORGANISM: Homo sapiens

<400> SEQUENCE: 3

| | | | | | |
|---|---|---|---|---|---|
| tctgggcgtg | gggaggctga | gacacgggag | tgcatctact | acaacgccaa | ctgggagctg | 60 |
| gagcgcacca | accagagcgg | cctggagcgc | tgcgaaggcg | agcaggacaa | gcggctgcac | 120 |
| tgctacgcct | cctggcgcaa | cagctctggc | accatcgagc | tcgtgaagaa | gggctgctgg | 180 |
| ctagatgact | caactgctac | gataggcag | gagtgtgtgg | ccactgagga | gaaccccag | 240 |
| gtgtacttct | gctgctgtga | aggcaacttc | tgcaacgagc | gcttcactca | tttgccagag | 300 |
| gctgggggcc | ggaagtcac | gtacgagcca | ccccgacag | ccccaccc | | 348 |

<210> SEQ ID NO 4
<211> LENGTH: 1539
<212> TYPE: DNA
<213> ORGANISM: Homo sapiens

<400> SEQUENCE: 4

| | | | | | |
|---|---|---|---|---|---|
| atgacggcgc | cctgggtggc | cctcgccctc | ctctggggat | cgctgtggcc | cggctctggg | 60 |
| cgtggggagg | ctgagacacg | ggagtgcatc | tactacaacg | ccaactggga | gctggagcgc | 120 |
| accaaccaga | gcggcctgga | gcgctgcgaa | ggcgagcagg | acaagcggct | gcactgctac | 180 |
| gcctcctggc | gcaacagctc | tggcaccatc | gagctcgtga | agaagggctg | ctggctagat | 240 |
| gacttcaact | gctacgatag | gcaggagtgt | gtggccactg | aggagaaccc | ccaggtgtac | 300 |
| ttctgctgct | gtgaaggcaa | cttctgcaac | gagcgcttca | ctcatttgcc | agaggctggg | 360 |
| ggcccggaag | tcacgtacga | gccacccccg | acagccccca | ccctgctcac | ggtgctggcc | 420 |
| tactcactgc | tgcccatcgg | gggccttttcc | ctcatcgtcc | tgctggcctt | tggatgtac | 480 |
| cggcatcgca | agccccccta | cggtcatgtg | gacatccatg | aggaccctgg | gcctccacca | 540 |
| ccatcccctc | tggtgggcct | gaagccactg | cagctgctgg | agatcaaggc | tcggggcgc | 600 |
| tttggctgtg | tctggaaggc | ccagctcatg | aatgactttg | tagctgtcaa | gatcttccca | 660 |
| ctccaggaca | gcagtcgtg | gcagagtgaa | cgggagatct | tcagcacacc | tggcatgaag | 720 |
| cacgagaacc | tgctacagtt | cattgctgcc | gagaagcgag | gctccaacct | cgaagtagag | 780 |

```
ctgtggctca tcacggcctt ccatgacaag ggctccctca cggattacct caaggggaac    840
atcatcacat ggaacgaact gtgtcatgta gcagagacga tgtcacgagg cctctcatac    900
ctgcatgagg atgtgccctg gtgccgtggc gagggccaca agccgtctat tgcccacagg    960
gactttaaaa gtaagaatgt attgctgaag agcgacctca cagccgtgct ggctgacttt   1020
ggcttggctg ttcgatttga gccagggaaa cctccagggg acacccacgg acaggtaggc   1080
acgagacggt acatggctcc tgaggtgctc gagggagcca tcaacttcca gagagatgcc   1140
ttcctgcgca ttgacatgta tgccatgggg ttggtgctgt gggagcttgt gtctcgctgc   1200
aaggctgcag acggacccgt ggatgagtac atgctgccct tgaggaaga gattggccag    1260 caccttcgt tggaggagct gcaggaggtg gtggtgcaca agaagatgag gcccaccatt   1320
aaagatcact ggttgaaaca cccgggcctg gcccagcttt gtgtgaccat cgaggagtgc   1380
tgggaccatg atgcagaggc tcgcttgtcc gcgggctgtg tggaggagcg ggtgtccctg   1440
attcggaggt cggtcaacgg cactacctcg gactgtctcg tttccctggt gacctctgtc   1500
accaatgtgg acctgccccc taaagagtca agcatctaa                          1539

<210> SEQ ID NO 5
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220
```

```
Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 6
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
```

```
                225                 230                 235                 240

Pro Ser Arg Glu Glu Met Thr Lys Asn Gln Val Ser Leu Thr Cys Leu
                    245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 7
<211> LENGTH: 21
<212> TYPE: PRT
<213> ORGANISM: Apis sp.

<400> SEQUENCE: 7

Met Lys Phe Leu Val Asn Val Ala Leu Val Phe Met Val Val Tyr Ile
1               5                   10                  15

Ser Tyr Ile Tyr Ala
            20

<210> SEQ ID NO 8
<211> LENGTH: 22
<212> TYPE: PRT
<213> ORGANISM: Unknown
<220> FEATURE:
<223> OTHER INFORMATION: Description of Unknown: Tissue plasminogen
      activator leader sequence

<400> SEQUENCE: 8

Met Asp Ala Met Lys Arg Gly Leu Cys Cys Val Leu Leu Leu Cys Gly
1               5                   10                  15

Ala Val Phe Val Ser Pro
            20

<210> SEQ ID NO 9
<211> LENGTH: 20
<212> TYPE: PRT
<213> ORGANISM: Unknown
<220> FEATURE:
<223> OTHER INFORMATION: Description of Unknown: Native leader
      sequence

<400> SEQUENCE: 9

Met Gly Ala Ala Ala Lys Leu Ala Phe Ala Val Phe Leu Ile Ser Cys
1               5                   10                  15

Ser Ser Gly Ala
            20

<210> SEQ ID NO 10
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
```

| | |
|---|---|
| atggatgcaa tgaagagagg gctctgctgt gtgctgctgc tgtgtggagc agtcttcgtt | 60 |
| tcgcccggcg cctctgggcg tggggaggct gagacacggg agtgcatcta ctacaacgcc | 120 |
| aactgggagc tggagcgcac caaccagagc ggcctggagc gctgcgaagg cgagcaggac | 180 |
| aagcggctgc actgctacgc ctcctggcgc aacagctctg gcaccatcga gctcgtgaag | 240 |
| aagggctgct ggctagatga cttcaactgc tacgataggc aggagtgtgt ggccactgag | 300 |
| gagaaccccc aggtgtactt ctgctgctgt gaaggcaact tctgcaacga gcgcttcact | 360 |
| catttgccag aggctggggg cccggaagtc acgtacgagc caccccgac agcccccacc | 420 |
| ggtggtggaa ctcacacatg cccaccgtgc ccagcacctg aactcctggg gggaccgtca | 480 |
| gtcttcctct tccccccaaa acccaaggac accctcatga tctcccggac ccctgaggtc | 540 |
| acatgcgtgg tggtggacgt gagccacgaa gaccctgagg tcaagttcaa ctggtacgtg | 600 |
| gacggcgtgg aggtgcataa tgccaagaca aagccgcggg aggagcagta caacagcacg | 660 |
| taccgtgtgg tcagcgtcct caccgtcctg caccaggact ggctgaatgg caaggagtac | 720 |
| aagtgcaagg tctccaacaa agccctccca gtccccatcg agaaaaccat ctccaaagcc | 780 |
| aaagggcagc cccgagaacc acaggtgtac accctgcccc catcccggga ggagatgacc | 840 |
| aagaaccagg tcagcctgac ctgcctggtc aaaggcttct atcccagcga catcgccgtg | 900 |
| gagtgggaga gcaatgggca gccggagaac aactacaaga ccacgcctcc cgtgctggac | 960 |
| tccgacggct ccttcttcct ctatagcaag ctcaccgtgg acaagagcag gtggcagcag | 1020 |
| gggaacgtct tctcatgctc cgtgatgcat gaggctctgc acaaccacta cacgcagaag | 1080 |
| agcctctccc tgtctccggg taaatga | 1107 |

<210> SEQ ID NO 11
<211> LENGTH: 6
<212> TYPE: PRT
<213> ORGANISM: Homo sapiens

<400> SEQUENCE: 11

Gly Arg Gly Glu Ala Glu
1               5

<210> SEQ ID NO 12
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
                20                  25                  30

Gly Glu Gln Asp Lys Arg Leu His Cys Tyr Ala Ser Trp Arg Asn Ser
            35                  40                  45

Ser Gly Thr Ile Glu Leu Val Lys Lys Gly Cys Trp Leu Asp Asp Phe
        50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro

```
                100                 105                 110
Thr Ala Pro Thr Gly Gly Thr His Thr Cys Pro Pro Cys Pro Ala
        115                 120                 125
Pro Glu Leu Leu Gly Gly Pro Ser Val Phe Leu Phe Pro Pro Lys Pro
    130                 135                 140
Lys Asp Thr Leu Met Ile Ser Arg Thr Pro Glu Val Thr Cys Val Val
145                 150                 155                 160
Val Asp Val Ser His Glu Asp Pro Glu Val Lys Phe Asn Trp Tyr Val
                165                 170                 175
Asp Gly Val Glu Val His Asn Ala Lys Thr Lys Pro Arg Glu Glu Gln
                180                 185                 190
Tyr Asn Ser Thr Tyr Arg Val Val Ser Val Leu Thr Val Leu His Gln
            195                 200                 205
Asp Trp Leu Asn Gly Lys Glu Tyr Lys Cys Lys Val Ser Asn Lys Ala
        210                 215                 220
Leu Pro Val Pro Ile Glu Lys Thr Ile Ser Lys Ala Lys Gly Gln Pro
225                 230                 235                 240
Arg Glu Pro Gln Val Tyr Thr Leu Pro Pro Ser Arg Glu Glu Met Thr
                245                 250                 255
Lys Asn Gln Val Ser Leu Thr Cys Leu Val Lys Gly Phe Tyr Pro Ser
            260                 265                 270
Asp Ile Ala Val Glu Trp Glu Ser Asn Gly Gln Pro Glu Asn Asn Tyr
        275                 280                 285
Lys Thr Thr Pro Pro Val Leu Asp Ser Asp Gly Ser Phe Phe Leu Tyr
290                 295                 300
Ser Lys Leu Thr Val Asp Lys Ser Arg Trp Gln Gln Gly Asn Val Phe
305                 310                 315                 320
Ser Cys Ser Val Met His Glu Ala Leu His Asn His Tyr Thr Gln Lys
                325                 330                 335
Ser Leu Ser Leu Ser Pro Gly Lys
            340

<210> SEQ ID NO 13
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 13

Thr His Thr Cys Pro Pro Cys Pro Ala Pro Glu Leu Leu Gly Gly Pro
1               5                   10                  15
Ser Val Phe Leu Phe Pro Pro Lys Pro Lys Asp Thr Leu Met Ile Ser
            20                  25                  30
Arg Thr Pro Glu Val Thr Cys Val Val Xaa Val Ser His Glu Asp
        35                  40                  45
```

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 14
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asp Ala Met Lys Arg Gly Leu Cys Cys Val Leu Leu Leu Cys Gly
1                5                  10                  15

Ala Val Phe Val Ser Pro Gly Ala Ala Glu Thr Arg Glu Cys Ile Tyr
                 20                  25                  30

Tyr Asn Ala Asn Trp Glu Leu Glu Arg Thr Asn Gln Ser Gly Leu Glu
             35                  40                  45

Arg Cys Glu Gly Glu Gln Asp Lys Arg Leu His Cys Tyr Ala Ser Trp
 50                  55                  60

Arg Asn Ser Ser Gly Thr Ile Glu Leu Val Lys Lys Gly Cys Trp Leu
 65                  70                  75                  80

Asp Asp Phe Asn Cys Tyr Asp Arg Gln Glu Cys Val Ala Thr Glu Glu
                 85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

```
Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 15
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 15
atggatgcaa tgaagagagg gctctgctgt gtgctgctgc tgtgtggagc agtcttcgtt      60
tcgcccggcg cc gct gag aca cgg gag tgc atc tac tac aac gcc aac tgg     111
              Ala Glu Thr Arg Glu Cys Ile Tyr Tyr Asn Ala Asn Trp
                1               5                  10 gag ctg gag cgc acc aac cag agc ggc ctg gag cgc tgc gaa ggc gag        159
Glu Leu Glu Arg Thr Asn Gln Ser Gly Leu Glu Arg Cys Glu Gly Glu
 15                  20                  25 cag gac aag cgg ctg cac tgc tac gcc tcc tgg cgc aac agc tct ggc        207
Gln Asp Lys Arg Leu His Cys Tyr Ala Ser Trp Arg Asn Ser Ser Gly
 30                  35                  40                  45 acc atc gag ctc gtg aag aag ggc tgt tgg cta gat gac ttc aac tgc        255
Thr Ile Glu Leu Val Lys Lys Gly Cys Trp Leu Asp Asp Phe Asn Cys
                 50                  55                  60 tac gat agg cag gag tgt gtg gcc act gag gag aac ccc cag gtg tac        303
Tyr Asp Arg Gln Glu Cys Val Ala Thr Glu Glu Asn Pro Gln Val Tyr
             65                  70                  75 ttc tgc tgc tgt gaa ggc aac ttc tgc aac gag cgc ttc act cat ttg        351
Phe Cys Cys Cys Glu Gly Asn Phe Cys Asn Glu Arg Phe Thr His Leu
         80                  85                  90 cca gag gct ggg ggc ccg gaa gtc acg tac gag cca ccc ccg aca            396
Pro Glu Ala Gly Gly Pro Glu Val Thr Tyr Glu Pro Pro Thr
```

|  |  |  |  |
|---|---|---|---|
| 95 | 100 | 105 |  |
| ggtggtggaa | ctcacacatg | cccaccgtgc ccagcacctg aactcctggg gggaccgtca | 456 |
| gtcttcctct | tccccccaaa | acccaaggac accctcatga tctcccggac ccctgaggtc | 516 |
| acatgcgtgg | tggtggacgt | gagccacgaa gaccctgagg tcaagttcaa ctggtacgtg | 576 |
| gacggcgtgg | aggtgcataa | tgccaagaca aagccgcggg aggagcagta caacagcacg | 636 |
| taccgtgtgg | tcagcgtcct | caccgtcctg caccaggact ggctgaatgg caaggagtac | 696 |
| aagtgcaagg | tctccaacaa | agccctccca gcccccatcg agaaaaccat ctccaaagcc | 756 |
| aaagggcagc | cccgagaacc | acaggtgtac accctgcccc catcccggga ggagatgacc | 816 |
| aagaaccagg | tcagcctgac | ctgcctggtc aaaggcttct atcccagcga catcgccgtg | 876 |
| gagtgggaga | gcaatgggca | gccggagaac aactacaaga ccacgcctcc cgtgctggac | 936 |
| tccgacggct | ccttcttcct | ctatagcaag ctcaccgtgg acaagagcag gtggcagcag | 996 |
| gggaacgtct | tctcatgctc | cgtgatgcat gaggctctgc acaaccacta cacgcagaag | 1056 |
| agcctctccc | tgtccccggg | taaatga |  | 1083 |

<210> SEQ ID NO 16
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

|  |  |  |  |
|---|---|---|---|
| tcatttaccc | ggggacaggg | agaggctctt ctgcgtgtag tggttgtgca gagcctcatg | 60 |
| catcacggag | catgagaaga | cgttcccctg ctgccacctg ctcttgtcca cggtgagctt | 120 |
| gctatagagg | aagaaggagc | cgtcggagtc cagcacggga ggcgtggtct tgtagttgtt | 180 |
| ctccggctgc | ccattgctct | cccactccac ggcgatgtcg ctgggataga agcctttgac | 240 |
| caggcaggtc | aggctgacct | ggttcttggt catctcctcc cgggatgggg gcagggtgta | 300 |
| cacctgtggt | tctcggggct | gcccttggc tttggagatg gttttctcga tgggggctgg | 360 |
| gagggctttg | ttggagacct | tgcacttgta ctccttgcca ttcagccagt cctggtgcag | 420 |
| gacggtgagg | acgctgacca | cacggtacgt gctgttgtac tgctcctccc gcggctttgt | 480 |
| cttggcatta | tgcacctcca | cgccgtccac gtaccagttg aacttgacct cagggtcttc | 540 |
| gtggctcacg | tccaccacca | cgcatgtgac ctcagggggtc cgggagatca tgagggtgtc | 600 |
| cttgggtttt | gggggggaaga | ggaagactga cggtcccccc aggagttcag gtgctgggca | 660 |
| cggtgggcat | gtgtgagttc | caccacctgt cggggtggc tcgtacgtga cttccgggcc | 720 |
| cccagcctct | ggcaaatgag | tgaagcgctc gttgcagaag ttgccttcac agcagcagaa | 780 |
| gtacacctgg | gggttctcct | cagtggccac acactcctgc ctatcgtagc agttgaagtc | 840 |
| atctagccag | cagcccttct | tcacgagctc gatggtgcca gagctgttgc gccaggaggc | 900 |
| gtagcagtgc | agccgcttgt | cctgctcgcc ttcgcagcgc tccaggccgc tctggttggt | 960 |
| gcgctccagc | tcccagttgg | cgttgtagta gatgcactcc cgtgtctcag cggcgccggg | 1020 |
| cgaaacgaag | actgctccac | acagcagcag cacacagcag agccctctct tcattgcatc | 1080 |
| cat |  |  | 1083 |

<210> SEQ ID NO 17
<211> LENGTH: 368
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 17

```
Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```

<210> SEQ ID NO 18
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Gly Gly Gly Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Gly Gly Gly Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 20

His His His His His His
1               5

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Glu Thr Arg Glu Cys Ile Tyr Tyr Asn Ala Asn Trp Glu Leu Glu
1               5                   10                  15

Arg Thr Asn Gln Ser Gly Leu Glu Arg Cys Glu Gly Glu Gln Asp Lys
            20                  25                  30

Arg Leu His Cys Tyr Ala Ser Trp Arg Asn Ser Ser Gly Thr Ile Glu
        35                  40                  45

Leu Val Lys Lys Gly Cys Trp Leu Asp Asp Phe Asn Cys Tyr Asp Arg
    50                  55                  60

Gln Glu Cys Val Ala Thr Glu Glu Asn Pro Gln Val Tyr Phe Cys Cys
65                  70                  75                  80

Cys Glu Gly Asn Phe Cys Asn Glu Arg Phe Thr His Leu Pro Glu Ala
                85                  90                  95

Gly Gly Pro Glu Val Thr Tyr Glu Pro Pro Pro Thr
            100                 105
```